(12) United States Patent
Matousek

(10) Patent No.: US 8,692,990 B2
(45) Date of Patent: Apr. 8, 2014

(54) ILLUMINATION OF DIFFUSELY SCATTERING MEDIA

(75) Inventor: Pavel Matousek, Abingdon (GB)

(73) Assignee: The Science and Technology Facilities Council, Oxfordshire (GB)

( * ) Notice: Subject to any disclaimer, the term of this patent is extended or adjusted under 35 U.S.C. 154(b) by 960 days.

(21) Appl. No.: 12/531,265

(22) PCT Filed: Mar. 14, 2008

(86) PCT No.: PCT/GB2008/000919
§ 371 (c)(1),
(2), (4) Date: Sep. 14, 2009

(87) PCT Pub. No.: WO2008/110825
PCT Pub. Date: Sep. 18, 2008

(65) Prior Publication Data
US 2010/0110425 A1 May 6, 2010

(30) Foreign Application Priority Data
Mar. 15, 2007 (GB) .................................. 0705031.3

(51) Int. Cl.
*G01N 21/47* (2006.01)
*G01N 21/65* (2006.01)
*G01J 3/44* (2006.01)

(52) U.S. Cl.
CPC ............... *G01N 21/47* (2013.01); *G01N 21/65* (2013.01); *G01J 3/44* (2013.01)
USPC ........................................................ 356/301

(58) Field of Classification Search
None
See application file for complete search history.

(56) References Cited

U.S. PATENT DOCUMENTS

| 4,081,215 | A | * | 3/1978 | Penney et al. ................ 356/301 |
| 5,194,913 | A | | 3/1993 | Myrick et al. |
| 5,221,957 | A | * | 6/1993 | Jannson et al. ............... 356/301 |
| 5,258,825 | A | | 11/1993 | Reed et al. |
| 5,442,438 | A | * | 8/1995 | Batchelder et al. .......... 356/301 |
| 6,226,082 | B1 | | 5/2001 | Roe |
| 7,068,430 | B1 | * | 6/2006 | Clarke et al. ................. 359/589 |
| 2002/0133065 | A1 | * | 9/2002 | Lucassen et al. ............. 356/301 |
| 2003/0081206 | A1 | | 5/2003 | Doyle |
| 2003/0120137 | A1 | | 6/2003 | Pawluczyk |
| 2006/0146322 | A1 | * | 7/2006 | Komachi et al. ............. 356/301 |

FOREIGN PATENT DOCUMENTS

WO WO-2006/061565 A1 6/2006

OTHER PUBLICATIONS

Wax et al., Path-Length-resolved dynamic light scattering modeling the transitionfrom single to diffusive scattering, Aug. 20, 2001, Applied Optics/ vol. 40, No. 24, pp. 4222-4227.*
Matousek et al., "Subsurface Probing in Diffusely Scattering Media Using Spatially Offset Raman Spectroscopy", Applied Spectroscopy, vol. 59, No. 4, pp. 393-400, 2005.

(Continued)

*Primary Examiner* — Gregory J Toatley
*Assistant Examiner* — Juan D Valentin, II

(57) ABSTRACT

The invention provides a technique for increasing the illumination intensity of probe light in a diffusely scattering sample without increasing the power of the probe beam. Generally, an optical filter is used which permits a collimated probe beam of light to pass through to the sample, but which reflects back towards the sample much of the backscattered scattered probe light emerging at a wider range of angles. In particular embodiments a collimated laser beam is delivered to the sample through a multi-layer dielectric filter covering a portion of the sample. The filter is transmissive to the laser light at normal incidence, but reflective at shallower angles of incidence characteristic of the backscattered light.

51 Claims, 16 Drawing Sheets

(56) References Cited

OTHER PUBLICATIONS

Angel S.M et al., "Development of a Drug Assay Using Surface-Enhanced Raman Spectroscopy" Optical Fibers in Medicine, vol. 1201, pp. 469-473, XP002911097, 1990.

Myrick M. L. et al., "Comparison of some Fiber Optic Configurations for Measurement of Luminescence and Raman Scattering" Applied Optics, Vo. 29, No. 9, pp. 1333-1344, XP000102329, 1990.

Angel M.S. et al., "Simultaneous Multi-point Fiber-optic Raman Sampling for Chemical Process Control Using Diode Lasers and a CCD Detector" Chemical, Biochemical, and Environmental Fiber Sensors III, vol. 1587, pp. 219-231, XP002343749, 1991.

Myrick M. L. et al., "Elimination of Background in Fiber-Optic Raman Measurements" Society for Applied Spectroscopy, vol. 44, No. 4, pp. 565-570, XP000116784, 1990.

* cited by examiner

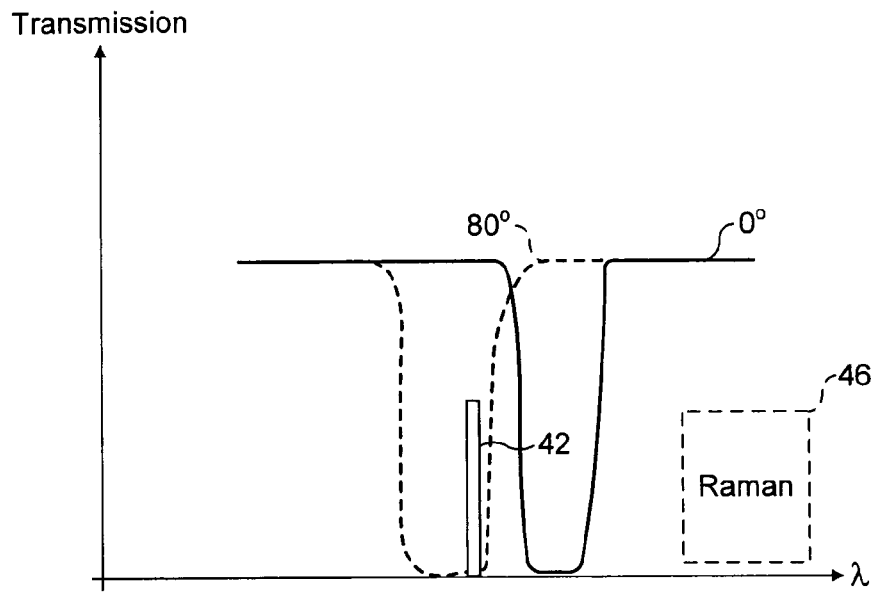
FIG. 7b
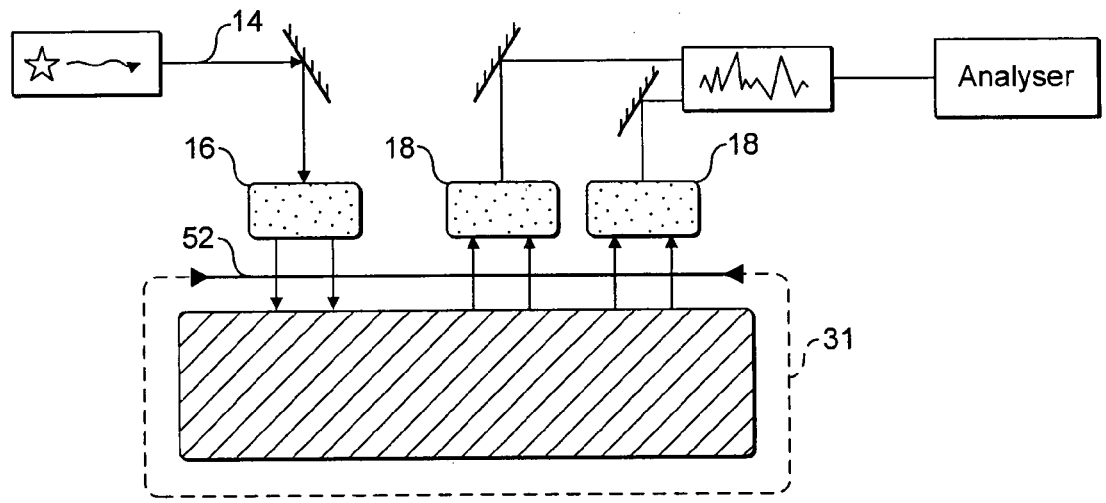
FIG. 8
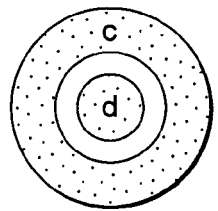 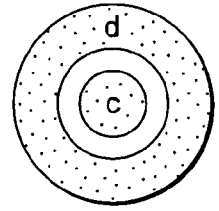
FIG. 9a          FIG. 9b

ILLUMINATION OF DIFFUSELY SCATTERING MEDIA

FIELD OF THE INVENTION

The invention relates generally to the illumination of diffusely scattering samples. In particular, the invention relates to techniques for reducing loss of incident light from within a sample, so that intensity of the incident light within the sample is increased. The invention may, for example, be applied to spectroscopy to increase the intensity of spectral features to be detected.

INTRODUCTION

Various analytical applications involve the spectroscopic analysis of diffusely scattering media. Examples include the probing of living tissue to determine tissue parameters such as bone composition as discussed in WO2006/61565, breast tissue, or blood glucose composition. The spectroscopic analysis of pharmaceutical tablets may be used to determine crystalline states or purity on a production line, in post production testing, and when screening for counterfeits. Other applications include the laboratory analysis of a wide variety of powdered samples, turbid fluids, translucent materials and so forth.

Raman spectroscopy, in which incident light is shifted in wavelength by inelastic scattering within a medium, is frequently used in such applications because of its high degree of chemical specificity, although infrared absorption and emission spectroscopy are also widely used. The cross section for Raman scattering is, however, particularly small, and obtaining a sufficiently high signal to noise ratio for spectral features of interest is challenging, especially in applications outside of the laboratory in which less sensitive equipment may be used. In many practical applications, incident light intensity must be limited, for example to avoid damage to living tissue, and exposure times may also be limited, for example on a production line, or where a measurement must be taken from a human patient in a reasonably short length of time. Of course, these and similar constraints also apply in the case of various types of infrared and other spectroscopic techniques.

Consequently, it is generally desirable to maximise the spectral signal obtained using a particular intensity or power of incident light, while minimising exposure times.

In other applications, it may be desirable to increase retention of incident light within a scattering sample for other reasons, such as to increase the rate of a chemical reaction triggered by the light, or to increase the amount of incident light escaping from the sample in the area where the light is introduced.

SUMMARY OF THE INVENTION

The invention seeks to address the above and other problems of the related prior art.

Various spectroscopic techniques and other applications require the directing of a beam of incident light into a sample. In some applications it is also desired to collect light scattered back out of the volume or from a surface of the sample, for example to detect spectral features in the collected light. Typically, the intensity of incident light at the surface or within the volume of a diffusely scattering sample, and hence the intensity of incident light scattered back out of the sample is greatest close to the point of application of the incident light.

The invention provides a method of increasing the illumination of a diffusely scattering sample by a beam of incident light, such as a laser beam or other substantially monochromatic beam of light, by covering a region of the sample with a delivery filter, and directing the beam to the sample through the filter. The filter has characteristics such that the light at the incident light wavelength which is diffusely scattered back from the sample to the filter at a wider range of angles of incidence than the incident beam is preferentially reflected back to the sample. Effectively, the filter acts as a unidirectional mirror, preventing loss of incident wavelength light, especially at the critical point of application to the sample of the incident light beam where intensities are greatest.

Some optical filter types, such as multi-layer dielectric filters have transmission and reflection characteristics which shift in wavelength, typically to shorter wavelengths, with increasing angle of incidence. The delivery filter may therefore be provided, for example, by using a multi-layer dielectric filter having a transmission region which matches the wavelength of the incident light at the angle of incidence of the beam, but which shifts away from the wavelength of the incident light at other angles of incidence. In this way, the incident beam, which is collimated or semi-collimated to a small range of angles of incidence passes through the filter into the sample, but the majority of diffusely reflected light, which returns at a range of angles significantly wider than the range of angles of incidence of the original beam, is reflected back towards the sample, with only a small fraction passing away from the sample through the filter.

An example delivery filter is a narrow band pass filter with a band pass region matching the incident light wavelength, to transmit the incident beam at normal incidence, but which increasingly reflects light of the same wavelength at larger angles of incidence. The same effect can be achieved using a notch filter or short wavelength transmission edge filter, having a reflection or low transmission region which lies just above the incident wavelength for normal incidence, but which shifts to cover the incident wavelength at larger angles of incidence.

According to one particular aspect, therefore, the invention provides a method of directing a beam of incident light to a diffusely scattering sample, comprising:

locating a delivery filter adjacent to the sample, or covering a region of the sample with the filter, the delivery filter having characteristics such that reflection of said incident light is dependent upon angle of incidence of said incident light at the filter; and directing a beam of said incident light through the delivery filter at a beam angle of incidence, which may preferably be approximately normal incidence, and to the sample, such that incident light diffusely scattered back from the sample towards the delivery filter is preferentially reflected by the filter back towards the sample.

According to another aspect, the invention provides a delivery filter having a transmission edge which lies to one side of the wavelength of the incident light at approximately normal incidence, for example less than 10° from perpendicular, thus permitting an incident beam to pass, and which lies at the other side of the wavelength of the incident light at shallower angles of incidence, for example greater than 30°, thus reflecting back diffusely scattered light emerging from a sample.

The invention also provides corresponding apparatus. For example, the delivery filter may be considered as an optical window, or an enclosure or cover, or may be part of a more extensive optical enclosure or cover for the sample having further optical components. An aspect of the invention then provides an optical cover for enhancing the intensity of incident light within a diffusely scattering sample comprising a delivery filter through which a beam of said incident light may be directed into the sample at a beam angle of incidence with said filter, the delivery filter having characteristics such that reflection of said incident light increases at angles of incidence away from the beam angle of incidence, such that incident light diffusely scattered out of the sample is preferentially reflected back into the sample by the delivery filter.

The delivery filter is preferably positioned adjacent to the sample, to maximise the return of incident light to the sample, and minimise escape of backscattered light around the edges of the filter. For example, if the filter has a diameter "d" then it may preferably be positioned within one diameter distance d from the sample, and more preferably half a diameter d/2, or more preferably still within a distance of about d/10. In practice, it may be preferable to locate the filter as close as possible to, for example touching, the sample. Typically, the filter may be parallel or approximately parallel to the underlying sample surface. Light may be collected by transmission back through the delivery filter, for example by using a filter having a transmission region covering the spectral features of interest, as discussed in detail below. Alternatively, a separate collection filter could be used having a suitable transmission region which preferably excludes the wavelength of the incident light for a wide range of angles of incidence.

The invention may be used in a variety of applications, such as to provide an optical enclosure around a pharmaceutical tablet or other object to be tested by spectroscopic analysis, or to provide a window to a tissue sample, or to part of a human or animal subject, through which a beam of incident light is directed.

BRIEF DESCRIPTION OF THE DRAWINGS

Embodiments of the invention will now be described, by way of example only, with reference to the accompanying drawings, of which:

FIGS. 7a and 7b show transmission characteristics for two example combined delivery/collection filters;

FIG. 8 illustrates the illumination of a sample by an incident beam and the collection of light at two separate spacings on the same side of the sample.

FIGS. 9a and 9b illustrate, in plan view, alternative configurations for delivery and collection filters disposed on the same side of a sample;

FIGS. 11b to 11f illustrate arrangements of a delivery filter 212, a collection filter 214, and mirrored surfaces 216 around the sample of FIG. 11a;

FIG. 15 illustrates a geometry of a central delivery filter and surrounding annular collection region applied to the model sample of FIG. 11a;

DETAILED DESCRIPTION OF PREFERRED EMBODIMENTS

Figure 1:
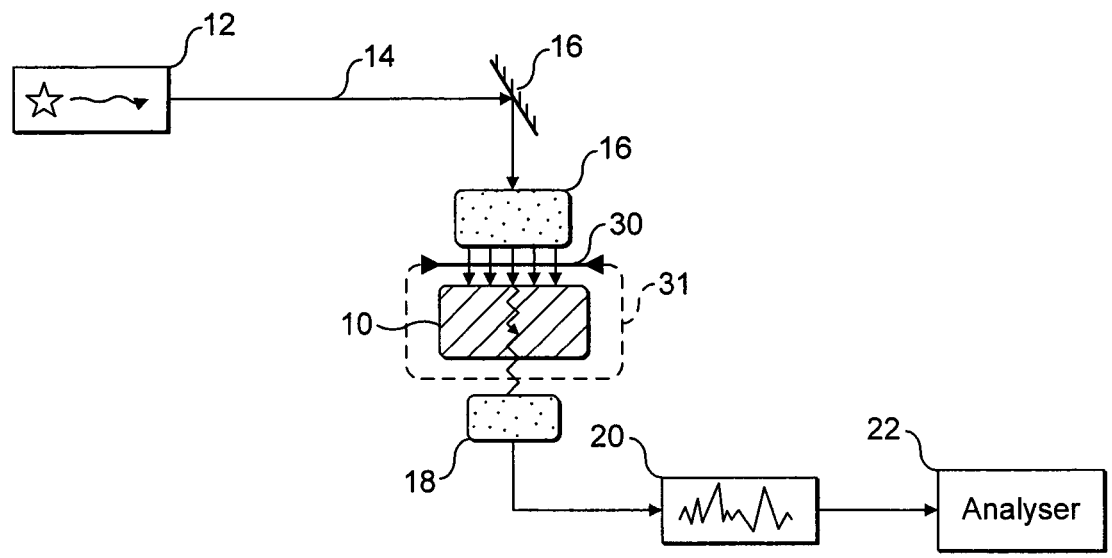
FIG. 1 illustrates schematically the illumination by, a incident beam 14 of a sample 10 through a delivery filter 30, and collection of scattered light for spectral analysis.

Referring to FIG. 1 there is shown, schematically, apparatus for determining characteristics of a diffusely scattering or turbid sample 10 using spectroscopy. In this particular example transmission Raman spectroscopy is used, although other techniques such as infrared absorption or fluorescence spectroscopy could be used.

A laser 12 forms an incident beam (probe beam) of laser light 14 which is directed towards the sample 10 by delivery optics 16. The beam enters the sample, and after scattering within the sample some photons are collected by collection optics 18. One or more spectral components of the collected light are detected by detector 20, such as a spectrometer, and results of the detection may typically be passed to a computer or other analyser device 22 for data storage and/or interpretation. In particular, photons which have been inelastically Raman scattered to different wavelengths within the diffusely scattering sample may be detected and analysed.

For many applications, especially in Raman spectroscopy for which the scattering cross sections are small, a high probe beam intensity is desired to increase the intensity of the spectral components to be detected. However, this may cause damage to the sample. An alternative approach, therefore, is to use a long exposure time, although this may be impractical for other reasons, for example the time available to make a measurement may be small such as on a production line. Another option to improve the collected spectral signal is to use a probe beam of higher cross sectional area. In the example of FIG. 1 this latter option has been used with the delivery optics delivering a wide diameter beam to the sample to increase total beam power without unduly increasing beam intensity.

A delivery filter 30 is positioned adjacent to, and may even be in contact with, the sample, to form, or partly form an at least partial optical enclosure 31 of or optical cover over the sample, and the probe beam is directed into the sample through this delivery filter. The filter has transmission characteristics which allow the probe beam to pass through the filter and into the sample, but which tend to block the return of probe light scattered back from the sample. A substantial portion, for example at least 50%, of the probe light scattering out of the sample is instead reflected by the delivery filter back into the sample, thereby increasing the intensity of probe light within the sample, and thereby the strength of the spectral components in the collected light which are to be detected.

Preferably this is achieved with only a minimal reduction in the power of the beam as it initially passes through the filter.

Figure 2A:
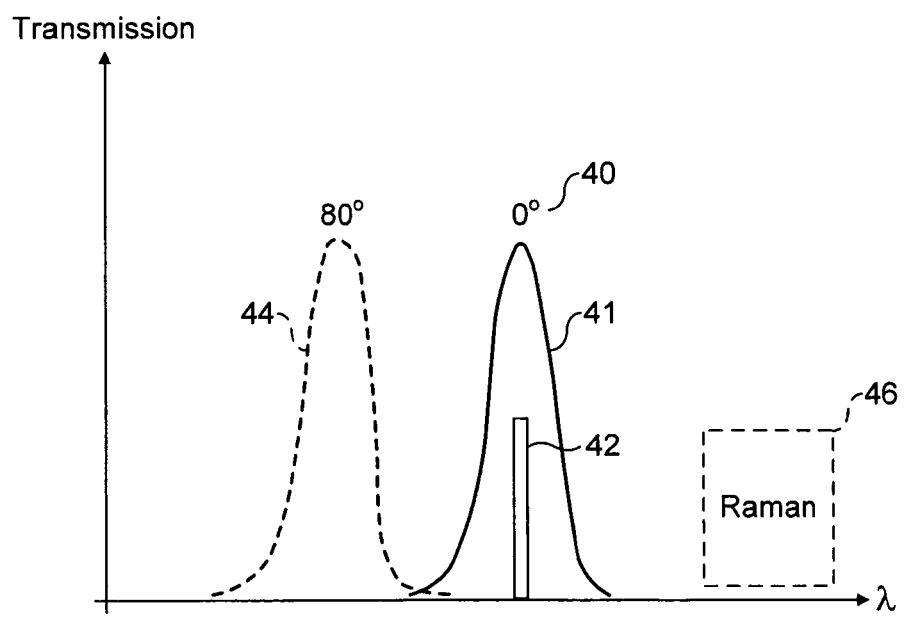
FIGS. 2a and 2b show transmission characteristics for two example delivery filters.

The desired characteristics of the delivery filter may be provided by a filter having transmission and/or reflection characteristics which shift in wavelength depending upon the angle of incidence of light at the filter, and example characteristics of such a filter are shown in FIG. 2a. The transmission characteristic for photons arriving at the filter at normal incidence is shown by the solid curve 40, which defines an approximately Gaussian transmission window. In this example the centre of the transmission window is coincident with the wavelength of the probe laser light 42, although this is not strictly necessary. For higher angles of incidence the transmission window moves to smaller wavelengths, for example as shown by the broken curve 44 for a 90 degree angle of incidence. As can be seen from the figure, probe light scattered back out of the sample and returning to the delivery filter at angles of incidence of greater than a few degrees away from normal will be reflected back into the sample, increasingly for higher angles of incidence, rather than being transmitted away from the sample through the delivery filter. The same effect is achieved by using the short wavelength transmission edge filter of FIG. 2b, with the edge wavelength matched to transmit light of the probe beam wavelength at the beam angle of incidence at the filter, and to reflect light of the same probe beam wavelength at larger angles of incidence.

The transmission window of FIG. 2a may be conveniently termed a probe light (or incident light) transmission feature, which shifts to shorter wavelengths away from the probe wavelength, for increasing angles of incidence. The low transmission region to the long wavelength side of the transmission window may similarly be termed an incident light reflection feature.

Figure 2B:
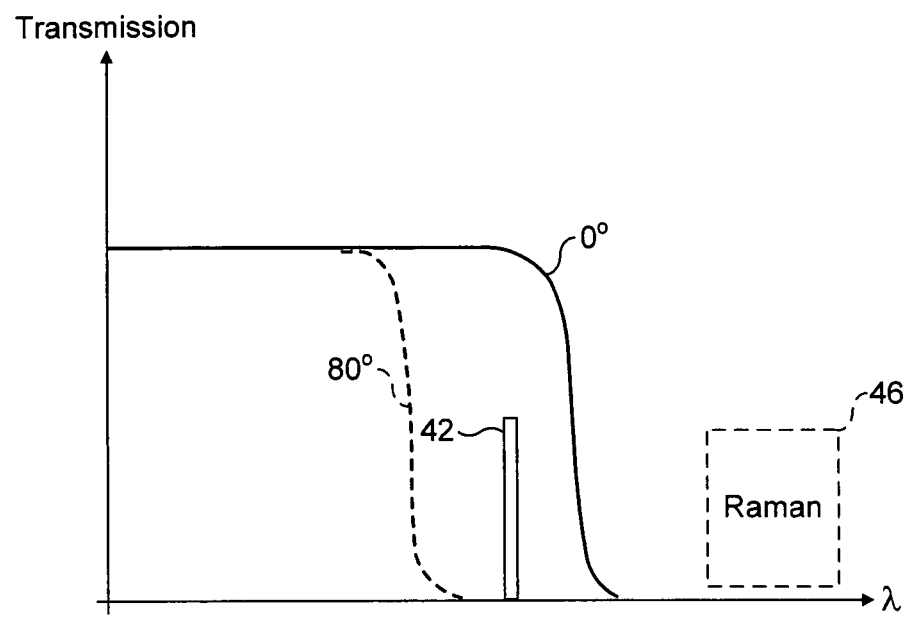

In FIG. 2b the transmission feature is provided by the long wavelength end of the transmission window, and the reflection feature by the low transmission region immediately beyond the edge.

The desired characteristics of the delivery filter may also be expressed in terms of a transmission edge 41 characteristic positioned to one side of the incident light wavelength band, close to normal incidence, and lying at the other side of the incident light wavelength at greater than a threshold angle of incidence, which could be 10°, 20° or other angles away from perpendicular, depending on the breadth of the incident light waveband, the type of filter used, and so on.

For the described mechanism to be effective it is necessary to use a probe beam which is collimated or at least semi-collimated so as to have a significantly smaller average angle of incidence at the filter than the average angle of incidence of beam photons subsequently scattered back out of the sample towards the delivery filter. Typically, the beam photons should have an average incidence angle of less than about 10 degrees in the presently described examples.

A typical wavelength range of Stokes shifted Raman scattered spectral features to be detected and analysed by the arrangement of FIG. 1 is shown as broken box 46 in FIGS. 2a and 2b. It can be seen that the filter characteristics have the additional benefit of blocking, and preferably reflecting back into the sample, Raman scattered photons, for subsequent collection by the collection optics.

A delivery filter having suitable characteristics may be provided by a dielectric multilayer filter, otherwise known as a thin-film interference filter, and in particular a narrow band pass filter of this type. Suitable filters are manufactured, for example, by Semrock, Inc., with information available at http://www.semrock.com. A catalogue MaxLine® Laser-Line narrow band pass filter or short wavelength pass edge filter could be used. Suitable band pass filters currently available from Semrock, Inc. have band pass widths from about 1.2 nm to 4.0 nm over a corresponding band pass range of close to 325 nm to 1064 nm.

The spectral shift of a multilayer dielectric filter as a function of angle of incidence can be derived from the following formula:

$$\lambda = \lambda_o \sqrt{1 - (\sin\Theta/n_{\text{eff}})^2}$$

Figure 3:
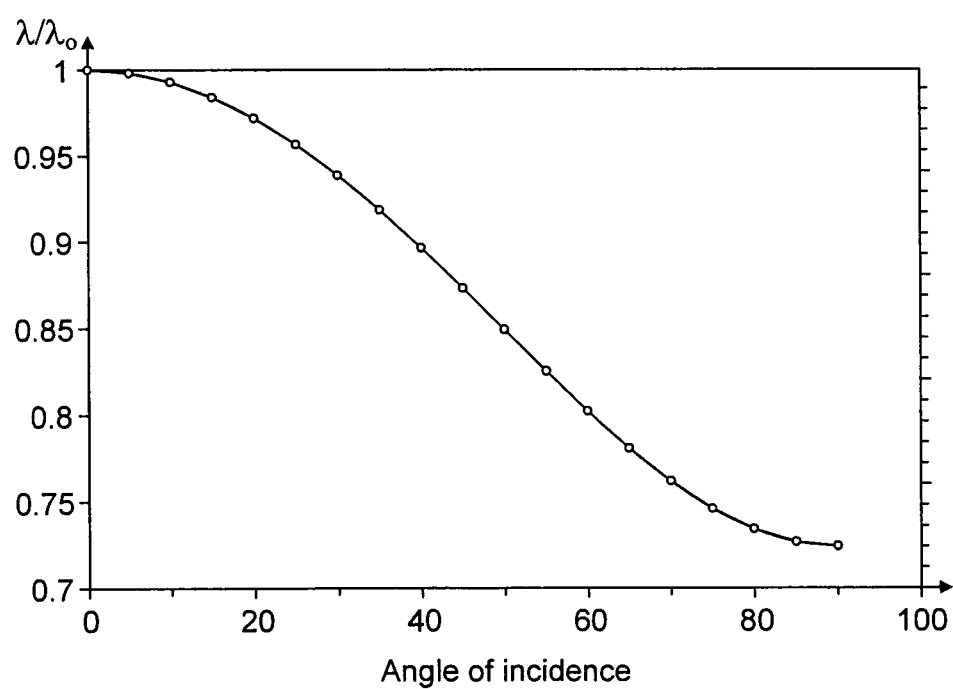
FIG. 3 shows the wavelength of the transmission feature of a narrow band pass dielectric filter at various angles of incidence, as a ratio with the wavelength of the transmission window at normal incidence.

In this formula, $\lambda_o$ is the wavelength of a spectral feature of the filter at the normal incidence and $\lambda$ is the new wavelength of the feature for photon incidence angle $\Theta$, $n_{\text{eff}}$ is the effective refractive index which is the refractive index of the filter medium/ambient refractive index (eg air). The formula inherently implies that only blue shifts are possible as the square root term is always smaller or equal to 1. FIG. 3 illustrates the dependence of $\lambda/\lambda_o$ on the angle of incidence. The plot assumes a constant value of the refractive index, set to 1.45, which corresponds to the refractive index of fused silica at ~800 nm. The ambient medium is assumed to be air.

From the above formula it can be estimated that a 10 degree tilt away from the normal incidence of the impacting photons results in a shift of the central wavelength of a band pass filter by about 6 nm. This is sufficiently far away from the laser wavelength for a typical narrow-band pass filter to result in the reflection, rather than transmission, of photons emerging from the sample at this or higher angles. Based on a simple geometric consideration, assuming that all of the photons impacting at the filter within a 10 degree half angle cone, and those at larger angles are reflected, then only about 1.5% of the photons emerging isotropically from the sample would be transmitted through the filter, and the remaining 98.5% would be reflected back into the sample. This calculation reflects the very low absorption losses in dielectric and similar filters such that the transmission fraction T and reflection fraction R are related as T+R≈1.

A filter may be obtained which matches the particular wavelength of the probe beam 14, in which case the probe beam can be directed through the delivery filter at or close to normal incidence. In this way the solid angle of incidence at which light scattered from the sample is reflected is maximised. However, if the central transmission wavelength of the filter at normal incidence is lower than the probe beam wavelength, then the beam may be directed at the delivery filter at a non-normal incidence to give a better wavelength match. This will tend to increase the solid angle at which probe light transmission takes place, and reduce effectiveness of the delivery filter in returning scattered light to the sample.

In FIG. 2a the characteristics of a narrow band pass filter are shown. However, filters having other characteristics can be used such as a spectrally broader band pass filter having a steep long wavelength edge positioned to transmit the probe light at only low angles of incidence, a short wavelength transmitting edge filter used in the same way as illustrated in FIG. 2b, or any other filter having a similar effect.

In FIG. 1 the delivery filter is illustrated as a partial, or part of a partial or complete optical enclosure around the sample. Proximity of the delivery filter to the sample is important. To be effective, a significant proportion of the probe light scattered out of the sample should be reflected back into the sample by the delivery filter. Since in the examples given above the amount of reflection is dependent on angle of incidence, the delivery filter should preferably be no further away from the sample than the diameter of the filter, or the size of the sample, whichever is smaller, and more preferably no further away than one tenth of this distance. Typically distances of up to a few mm, for example less than 5 mm, may be appropriate.

Figure 4:
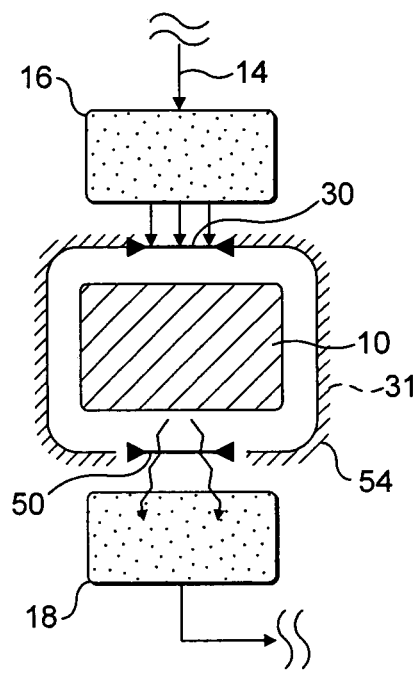
FIG. 4 illustrates a more complete optical enclosure extending that of FIG. 1 to include mirror surfaces 54 and a collection filter 50.

FIG. 4 illustrates a further developed optical enclosure disposed around the sample 10 of FIG. 1. Although not illustrated, the laser beam is delivered, and light collected and analysed in much the same way as in FIG. 1. The principal difference is that further optical elements have been added to the enclosure 31 close to the sample 10 in order to further increase the intensity of probe light within the sample, and to reduce the loss of those spectral components which are to be detected and analysed.

Disposed between the sample and the collection optics is an optional collection filter 50. This filter is selected to block the majority of probe light emerging from the sample towards the collection optics 18, and preferably to reflect at least a substantial portion of this probe light back into the sample. The filter is also selected to allow scattered light of longer wavelengths to pass, in particular photons which have been Stokes shifted by Raman scattering.

Figure 5:
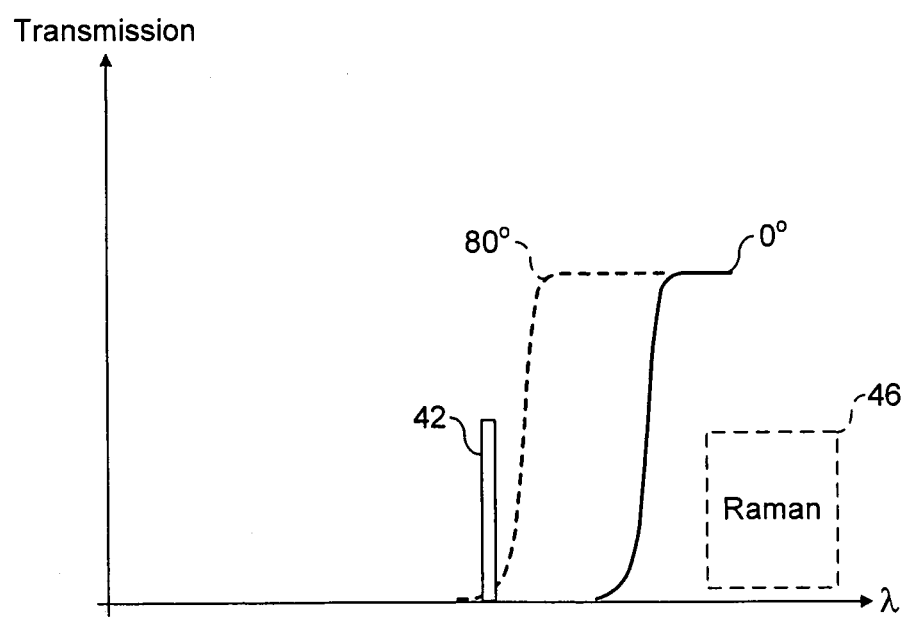
FIG. 5 shows transmission characteristics for an example collection filter.

Suitable transmission characteristics for the collection filter are illustrated in FIG. 5. It will be seen that the transmission curve has a steep edge between the probe wavelength 42 and the wavelengths of spectral interest 46, so that the filter reflects probe light back into the sample but allows Raman scattered photons to pass. If a filter having characteristics which shift to smaller wavelengths with increasing angle of incidence is used, then design constraints may result in probe light at higher angles of incidence passing through the filter in significant amounts. A further filter in the collection optics, such as a narrow band notch filter, may be used to eliminate any remaining photons of the original wavelength present in the collected light.

A long-wave-pass dielectric multi-layer edge filter may be used for the collection filter, for example a catalogue RazorEdge® filter currently manufactured by Semrock, Inc. Such filters are available with edges at a range of wavelengths from infrared to ultraviolet, with a pass band width of typically 100 nm to 1000 nm, and an edge transition width of between about 100 cm$^{-1}$ and 500 cm$^{-1}$. Of course, a filter of especially selected characteristics may be used if required.

To be effective in returning probe photons back into the sample, the edge of the collection filter characterised in FIG. 5 must be at a sufficiently longer wavelength than the probe wavelength 42 to permit the filter to reflect probe photons arriving at a wide range of angles, for example in the region of 1000 cm$^{-1}$ to 2000 cm$^{-1}$ above the probe wavelength. In practice, this may restrict the range of Raman spectral features detectable to wavelengths at least this much longer than the probe wavelength, for the collection filter to be effective in returning probe photons into the sample.

The optical enclosure 31 shown in FIG. 4 optically includes or is completed with one or more optically reflecting mirror surfaces 54 around the sample. There is no need for these surfaces to transmit either probe light or light to be collected, so elements reflecting at least at the probe wavelength and at the wavelengths of spectral components to be detected, over a wide range of angles of incidence should be used.

To maximise the effect of the cavity, the delivery and collection filters may be sized to cover only the areas needed for probe light delivery and light collection, with substantially all of the remaining enclosure provided by highly reflective mirrored surfaces.

Figure 6:
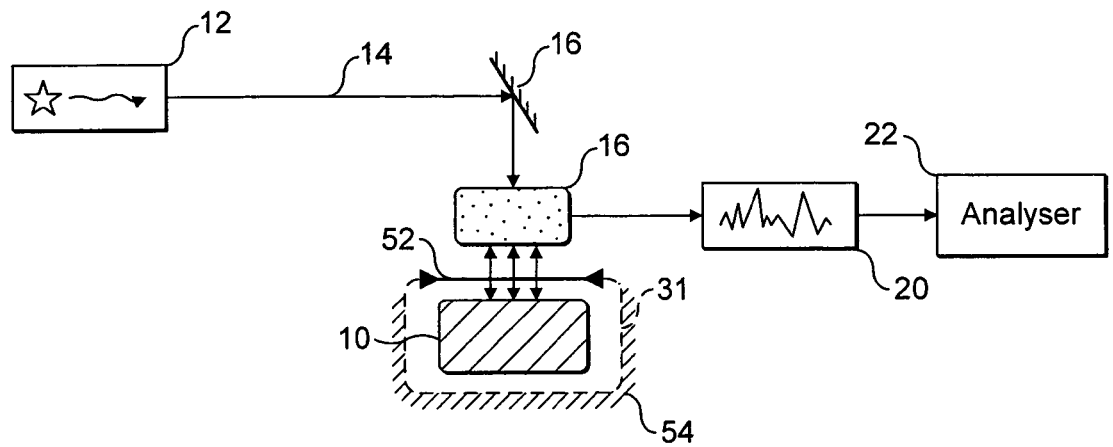
FIG. 6 shows an arrangement in which incident light delivery and collection use the same filter.

Some alternative embodiments and configurations using the invention are illustrated using FIGS. 6-9b. In FIG. 6 the laser beam 14 is delivered to and light is collected from the same part or surface of the sample 10. To achieve this a combined delivery/collection filter 52 is used to both transmit the probe beam to the sample and to transmit light to be analysed by detector 20 and analyser 22. The combined filter 52 is located proximal or adjacent to the sample in the same way as the delivery filter in the examples of FIGS. 1 and 3 to form at least part of an optical enclosure 31 for the sample. The enclosure may also present reflective or mirrored surfaces 54 to parts of the sample, and may additionally include a separate collection filter.

Figure 7A:
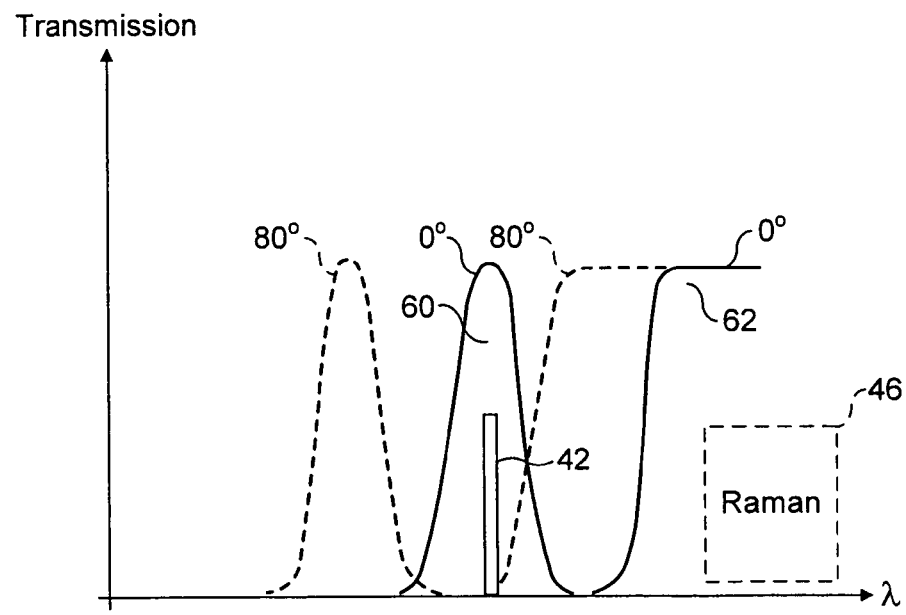

The combined filter 52 has characteristics which allow transmission of spectral features wanted for detection and analysis, while reflecting a significant portion of light having the wavelength of the probe beam back into the sample. Transmission characteristics of a suitable filter are presented in FIGS. 7a and 7b. The filter of FIG. 7a combines a narrow transmission window 60 coincident with the probe wavelength 42, shown in the figure as having an approximately Gaussian form, with a low-pass edge transmission window 62. In FIG. 7b a reflecting feature of a notch filter blocks wavelengths lying in a region between the probe wavelength 42 and the Raman spectral feature region 46. In both cases, the filter characteristics shift to shorter wavelengths as incidence angle is increased, as already described above, with the broken curves showing the transmission at an angle of 80 degrees. It can be seen that at all angles the Stokes shifted Raman spectral features in region 46 are transmitted through the filter to be collected and analysed. Probe wavelength light scattering out of the sample to the combined filter at angles away from normal incidence is reflected back into the sample to a large extent.

Filters having suitable characteristics similar to those shown in FIGS. 7a and 7b can be constructed using known thin-film interference filter techniques. Other types of filter construction and filters having other characteristics may also be used to achieve a combined delivery/collection filter. Such filters can also be used as a delivery only filter, although with unwanted loss of the Raman shifted light through the filter.

Although FIGS. 1 and 4 illustrate a transmission geometry where light is delivered and collected at opposing sides of a sample, and FIG. 6 illustrates a reflection geometry in which delivery and collection take place in the same or closely spaced regions, a range of other geometries may be used. In FIG. 8 a single combined delivery/collection filter 52 is used. Delivery optics 16 direct the probe laser beam 14 through a first region of the filter into the sample, and one or more separate collection optics 18 collect light transmitted through one or more further regions of the filter spaced from the first region. As described in WO2006/061566, this geometry can be used to determine spectral characteristics of the turbid sample from a controlled profile of depth. With a single collection optic the analyser can be arranged to reject surface spectral features if known in advance to select for spectral features from depth, while with multiple collection optics a deconvolution of spectral characteristics from different depths can be carried out using assumptions regarding the expected contributions from different depths depending on distance of collection from the delivery region.

In variations to the geometry of FIG. 8, one or more dedicated collection filters such as that discussed in connection with FIG. 5 are used between the sample and the collection optics. In FIG. 9a a central delivery filter (d) is surrounded by an annular, concentric collection filter (c). In FIG. 9b a central collection filter (c) is surrounded by an annular concentric delivery filter (d). The collection and delivery optics for such arrangements may conveniently comprise a bundle of optical fibres, for example as discussed in WO2006/061566. Clearly, various other geometries could be used. For example, either the delivery or the collection filter could be omitted, and various continuous and segmented shapes could be used for the regions.

Optical elements suitable for use as the described delivery filter, especially dielectric multilayer filters, are readily available commercially as flat elements. As described above, it is desirable for the filter to be located close to the surface of the sample, to maximise reflection by the filter of scattered incident light back towards the sample. Clearly, if the surface of the sample in the region of the delivery filter is strongly curved instead of flat, the effect of the invention may be reduced. FIGS. 10a to 10d illustrate ways in which the otherwise adverse effects of a curved sample surface may be mitigated.

Figure 10A:
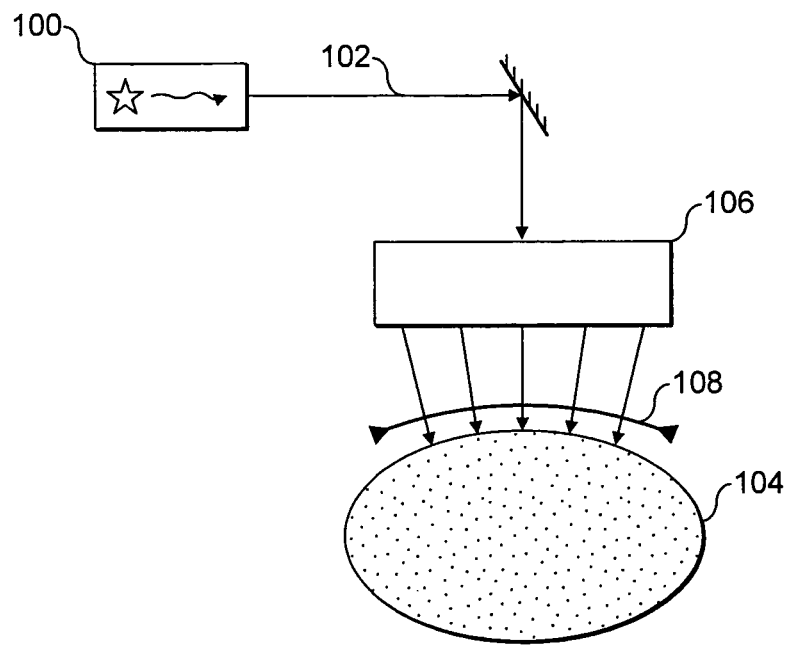
FIGS. 10a to 10d illustrate arrangements for applying the invention to a curved sample surface.

FIG. 10a shows, in cross section, a diffusively scattering sample 104 having a curved surface. An example of such a sample might be a pharmaceutical capsule or tablet. As in previous figures, a laser 100 forms an incident beam of laser light 102 which is directed towards the sample 104 by delivery optics 106. Collection optics, detector and analysis elements are not shown in FIG. 10a, but of course may be present as required. The incident beam enters the sample 104 through a delivery filter 108 which is itself curved so as to match, at least approximately, the surface of the underlying sample 104. The delivery filter has optical characteristics as described above, including the characteristic of preferentially allowing the incident beam to pass at angles close to normal to the filter, while reflecting back to the sample diffusely scattered light of the same wavelength emerging from the sample at a wider range of angles, for example beyond around 10° from perpendicular.

To provide optimal transmission of the incident beam through the curved delivery filter, the delivery optics 106 are adapted to form the beam such that the angle of incidence is close to normal across the surface of the filter. For a convex sample surface and delivery filter this might be achieved by an appropriate concave lens or suitably shaped mirror.

Figure 10B:
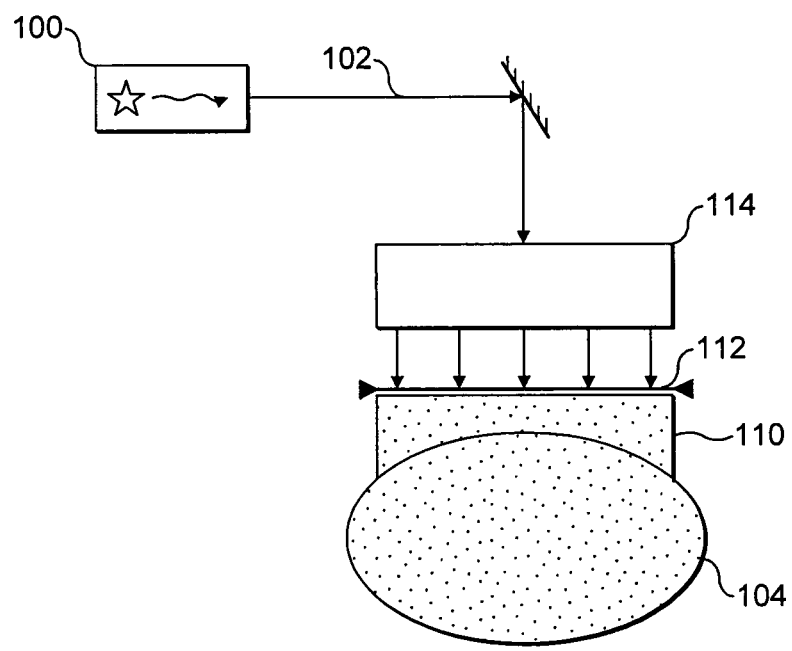

Because curved dielectric filters are likely to be expensive and more difficult to obtain or manufacture than flat filters, it would be desirable to adapt the invention for use on curved sample surfaces while still using a flat filter. In FIG. 10b this is achieved by disposing a diffusely scattering spacer element 110 between a sample surface and a flat delivery filter 112. The spacer element 110 may comprise, for example, an elastomer such as a silicon polymer containing isotropic scattering centres such as micrometer sized particles. The spacer element 110 may be rigid or semi rigid, and shaped to conform to the underlying curvature of the sample 104. Alternatively, the spacer element may be sufficiently flexible to conform to the sample 104, from a relaxed shape which is either an approximation to the sample, or a different shape such as a flat surface. An advantage of using an elastically deformable spacer element is that it may conform closely to the sample surface against which is pressed. An advantage of this arrangement is that the delivery optics 114 do not need to supply an appropriately converging or diverging beam, since only a collimated incident beam is required.

A variation on the described arrangement of FIG. 10b is to include in the spacer element 110 anisotropic scattering characteristics, favouring the sample to filter scattering direction. This can be achieved, for example, by including fibre elements, such as silica fibres, extending in this direction, mixed with diffusely scattering spherical micrometer-size particles.

Figure 10C:
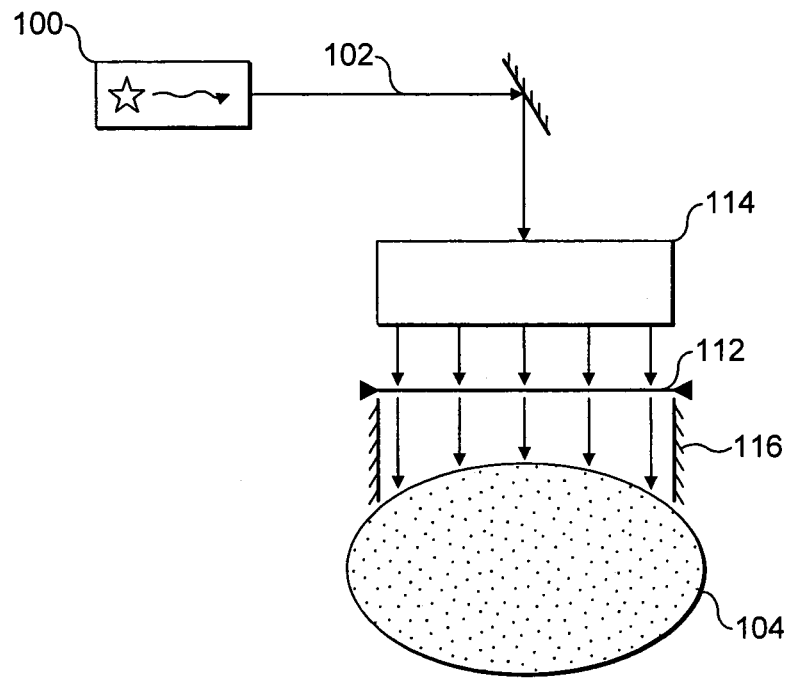

Another arrangement for adapting a flat delivery filter 112 to a curved sample 104, using peripheral mirrored guiding surfaces 116 is shown in FIG. 10c. The surface of the sample 104 to be covered by the delivery filter 112 is convex, and the resulting gap between the filter and the sample is provided with the peripheral mirrored guiding surfaces, so as to prevent or reduce the escape of diffusely scattered light emerging from the thereby enclosed sample surface, and to channel this light to the delivery filter, for reflection back towards the sample 104.

Typically, the peripheral mirrored guiding surfaces will be approximately perpendicular to the delivery filter, and extend around a circumference of the space between the filter and the curved surface of the sample to be covered. Such a peripheral mirrored guide is advantageous in providing improved coupling, without deformation or adaption, to a range of sample surface curvatures including flat surfaces.

Figure 10D:
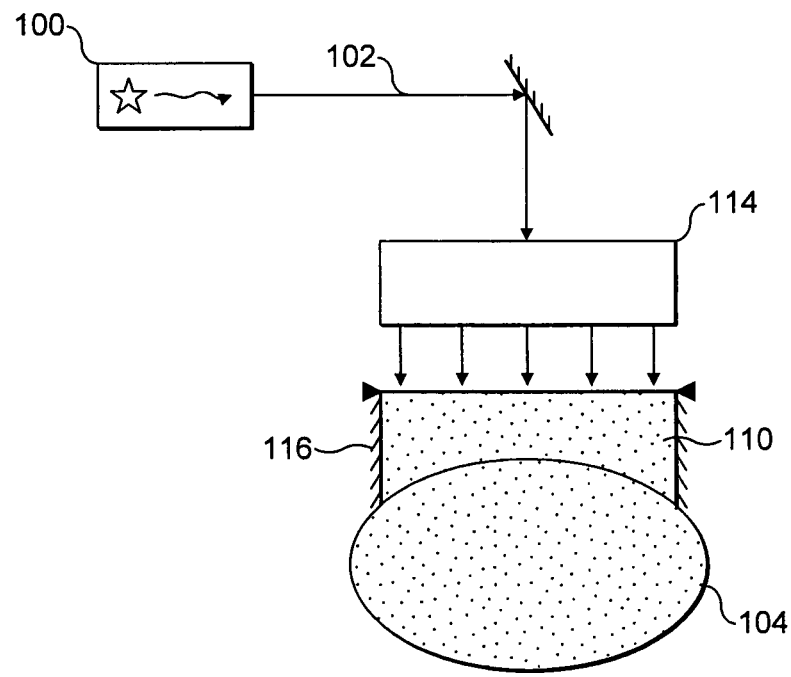

FIG. 10d illustrates an arrangement combining the approaches of FIGS. 10b and 10c, with the described spacer element 100 being provided with the described mirrored guiding surfaces 116 about its periphery.

Numerical Model

A numerical model already described in Matousek, P. et al., Applied Spectroscopy 59, 1485 (2005) was used to demonstrate the effectiveness of the optical enclosure 31 described above. Briefly, both elastically scattered probe beam photons and non-elastically scattered (eg Raman scattered) photons are individually followed as they propagate through a modelled medium in random walk-like fashion in three-dimensional space. A simplified assumption is made that in each step a photon propagates in a straight line over a distance t and thereafter its direction is fully randomised at the next scattering event. This is somewhat simplistic from the standpoint of individual scattering events which are often strongly biased towards the forward direction. However, for large numbers of scattering events, as of interest here, this simplification is justifiable with an appropriately chosen randomisation length. The propagation distance, t, over which the photon direction is randomised, can be crudely approximated as the transport length of the scattering medium $l_t$, which is defined as the average distance photons must travel within the sample before deviating significantly from their original direction of propagation.

Figure 11A:
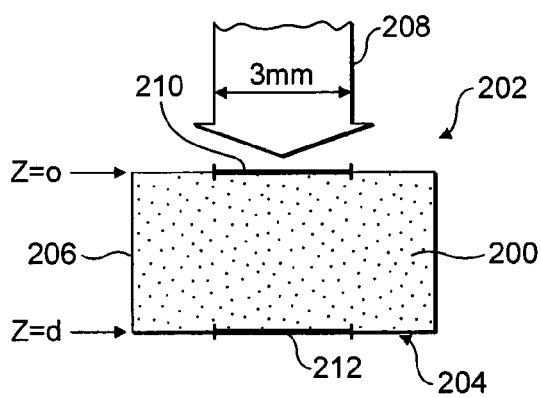
FIG. 11a illustrates geometry of a sample used in a mathematical model used to demonstrate the invention.

As shown in FIG. 11a, the model considers the sample 200 to be a homogeneous turbid medium having the shape of a short cylinder with a radius of 6 mm. A first air-medium interface 202 is located at a top circular surface with z=0, where z is a Cartesian coordinate normal to the interface plane. The other sample-to-air interfaces exist at the opposite circular surface 204 of the sample at a position z=d, where d is the sample thickness, and on the cylindrical side wall 206 of the sample. The thickness of the sample d was varied between simulations, from 0.5 mm to 6 mm in 0.5 mm steps.

The model assumes that all the probe photons are first placed at a depth equal to the transport length it and symmetrically distributed around the origin of the co-ordinate system x,y. The radius of the probe beam 208 of incident light is r=3 mm and the beam has uniform intensity, with a flat, 'top-hat' intensity profile with all the photons having equal probability of being injected into the sample at any point within the beam cross-section.

The numerical code was written in Mathematica 5.0 (Wolfram Research). 100,000 photons were propagated separately, each across an overall distance of 400 mm (2000 steps) which is in line with observed migration times in Raman spectroscopy. If not detected or lost from the medium within this propagation distance, the photons were assumed to be absorbed by the medium itself which might be the case in the presence of very weak absorption (OD ~1 per 40 cm).

The optical density accounting for the conversion of probe photons into Raman photons was set to 1 per 1000 mm. Although this value is higher than that of real conversion, it only affects the absolute number of Raman photons, and not the spatial dependencies of concern to a significant degree in the studied regime and was verified by varying this value up and down. The step size used was t=0.2 mm. This corresponds to powder particle sizes of 10 and 20 µm diameter for an anisotropy of 0.9 and 0.95, respectively. The calculations were repeated 10 times summing all the detected Raman photons in these repeated runs.

The model assumes two different collection geometries. In a first geometry, light is collected at the top sample surface from the same region 210 on the sample surface as the probe beam entry (backscattering geometry). In a second geometry, light is collected from the opposite surface of the sample from a congruent region 211 centred around the projection axis of the probe beam (transmission geometry). The model calculations were first performed for both the transmission and backscattering geometries assuming no filters or reflective elements.

Figure 11D:
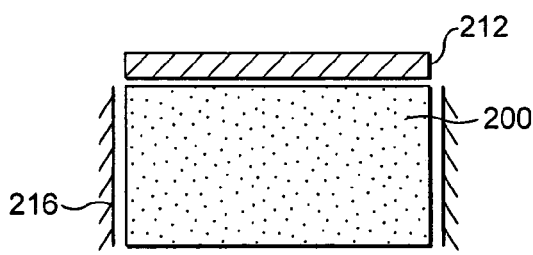
Figure 11B:
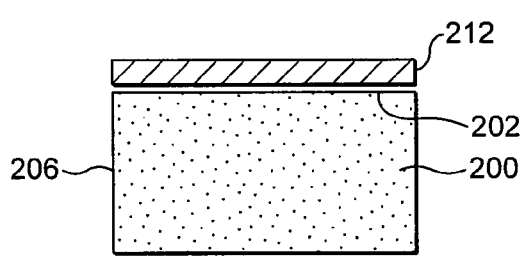
Figure 11E:
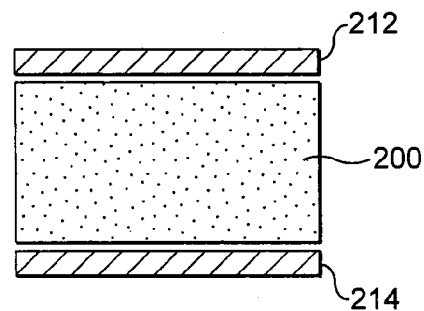
Figure 11C:
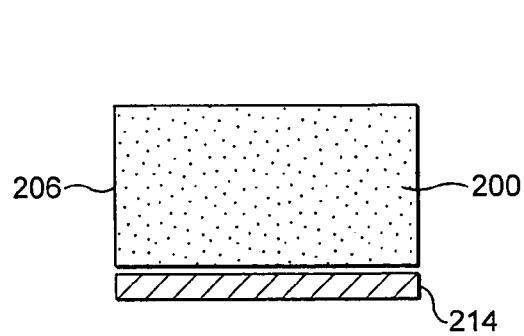

The transmission geometry calculation was then carried out with the presence of particular optical enclosure elements as illustrated in FIGS. 11b-11f. In FIG. 11b a delivery filter 212 is provided by a band pass filter transmitting all the probe photons from above and reflecting 95% of the probe and Raman photons from below. The delivery filter is positioned adjacent to the upper surface 202 of the sample, covering the whole surface. In FIG. 11c a collection filter 214 is provided by an edge filter transmitting all the Raman photons and reflecting 95% of the laser photons back into the turbid medium. The collection filter is positioned at the lower surface 204 of the sample, and there is no delivery filter at the upper surface.

In FIG. 11d the delivery filter 212 is provided, and the sidewall 206 of the sample is surrounded by a 100% reflective enclosure 216 to return both probe wavelength and Raman scattered photons into the sample, but no collection filter is used. In FIG. 11e, the delivery filter 212 and collection filter 214 are present, and in FIG. 11e all three components, including the sidewall mirrored reflective element, are present.

Figure 11F:
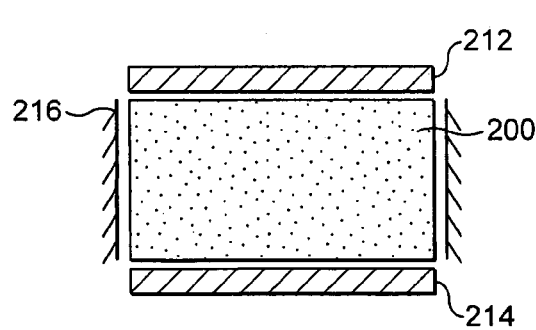
Figure 12A:
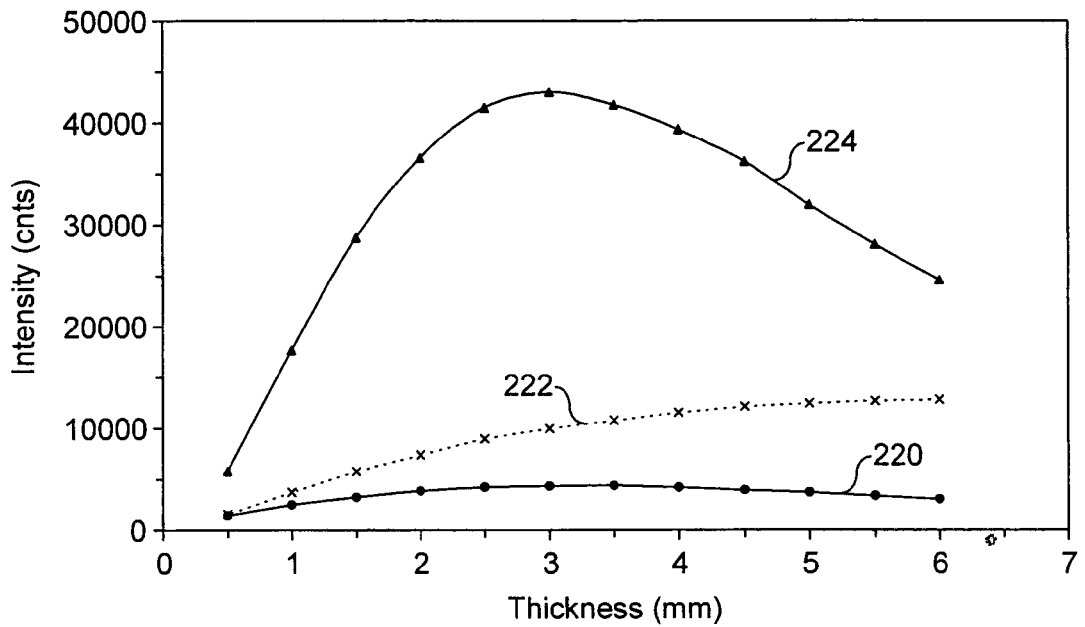
FIGS. 12a and 12b, 13a, 13b, 14a and 14b show calculated intensities of Raman scattered photons emerging from the sample of FIG. 11a according to various configurations of filters and mirrored surfaces used in the mathematical model, and related enhancement factors.
Figure 13A:
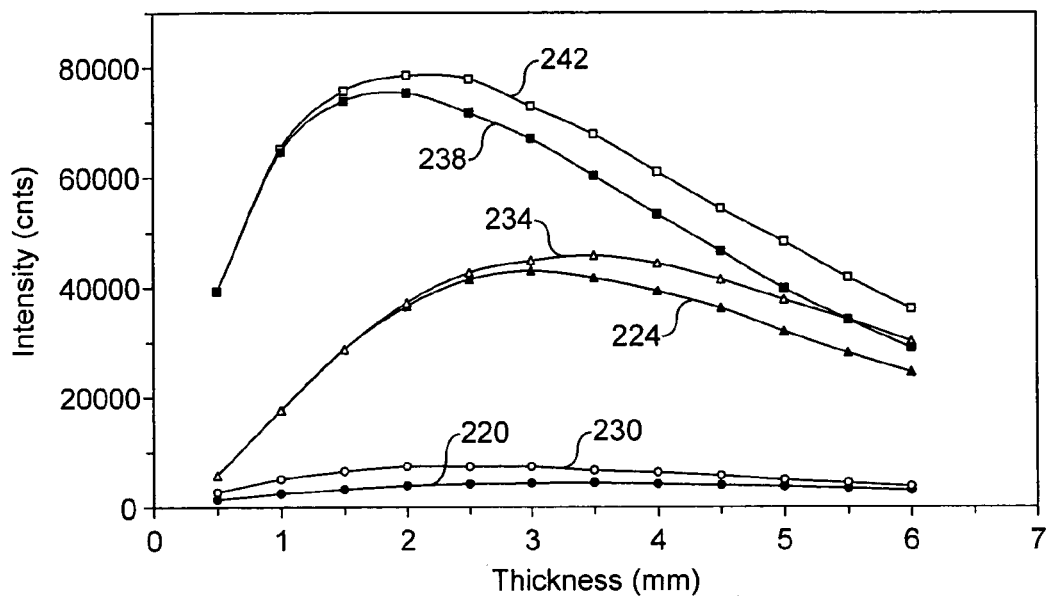

Results of the Monte Carlo simulations for the various transmission geometries of FIGS. 11b-11f are shown in FIGS. 12a and 13a, in which the ordinates represent counts of Raman scattered photons collected at the collection region 210 or 211, and the abscissae represent different thicknesses of sample. In FIG. 12a curve 220 results from the transmission geometry being used with no optical enclosure elements. Curve 222 results from the backscattering geometry being used, again with no enclosure elements.

The signal in the backscattering geometry is about 3 times higher than that for the transmission mode for a bare 4 mm thick sample, which is a typical thickness for a pharmaceutical tablet. The signal for the backscattering mode rises monotonically with increasing sample thickness, a behaviour observed experimentally previously. For the transmission geometry the signal intensity initially increases with the tablet thickness due to larger photons pathways available for the conversion of photons into Raman photons, but beyond about 3 mm the signal starts diminishing, an effect ascribed to increased lateral photon transport causing more photons to miss the collection aperture.

Figure 12B:
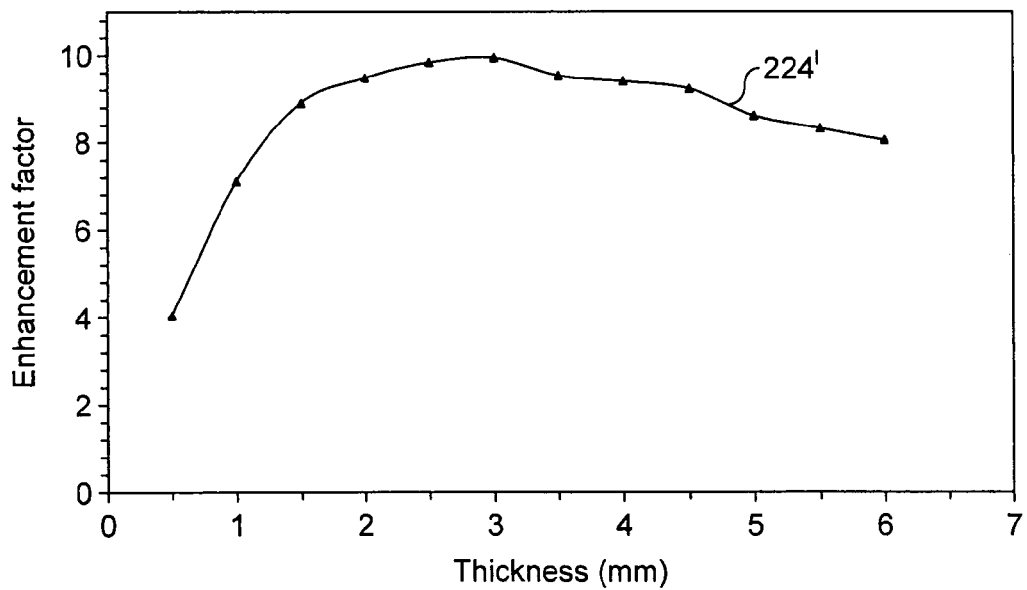

Curve 224 results from the transmission geometry being used with the arrangement illustrated in FIG. 11b, with the probe beam passing into the sample through delivery filter 212. The model predicts an enhancement of the transmission Raman signal collected at the opposite face by a factor of about 9.4 for a 4 mm thick sample. Interestingly, this signal level considerably exceeds even that of the backscattering Raman signal for the unenclosed sample. The ratio of the transmission geometry curves with and without the delivery filter (224, 222) is plotted as an "enhancement factor" 224' in FIG. 12b, which lies between about 8 and 10 across most of the thickness range above 1 mm.

In FIG. 13a, curve 220 again represents Raman scattered photons collected in a transmission geometry with no optical enclosure elements. Curve 230 results from the addition of collection filter 214, but no delivery filter 212, as illustrated in FIG. 11c. As shown in the corresponding enhancement factor curve 230' in FIG. 13b, the collection filter on its own gives rise to about a doubling of the detected Raman photons. This is a much weaker effect than use of the delivery filter alone, as expected because the largest photon loss in absence of any enclosure element is at the point of entry of the probe beam.

Figure 13B:
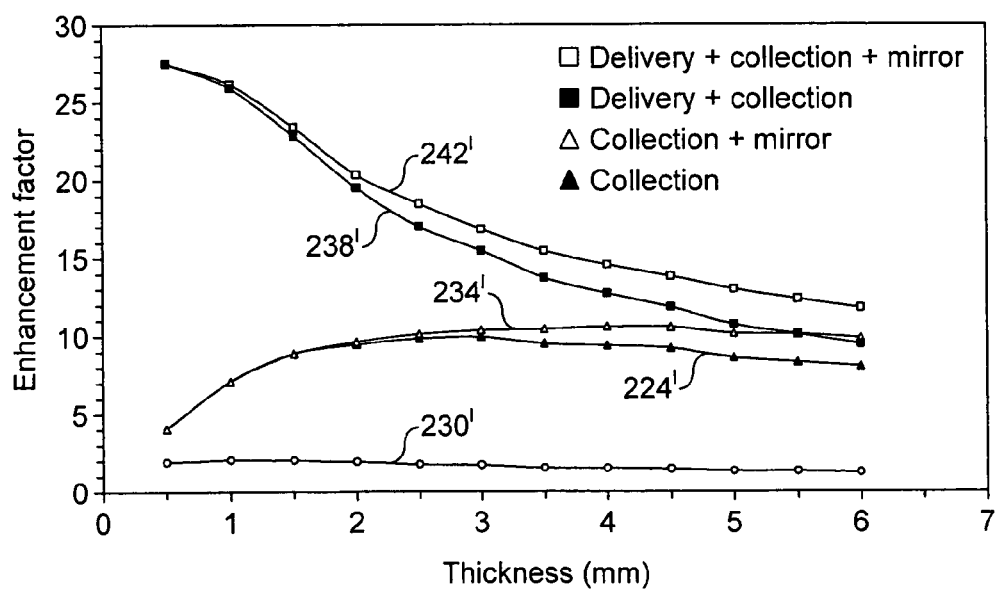

The delivery filter curve 224 of FIG. 12a is shown for comparison, and the modest increase in detected Raman intensity achieved by using the additional mirror sidewall mirror element as illustrated in FIG. 11d is shown as curve 234 (and as enhancement factor curve 234' in FIG. 13b). For sample objects 200 of reduced diameter or increased thickness the sidewall mirror enclosure would provide larger enhancements.

Curve 238 is for the configuration of FIG. 11e, where the delivery and collection filters are used but without the mirrored sidewall element. The enhancement factor 238' plotted in FIG. 13b, is about 27.5 for the minimum 0.5 mm thick sample, falling continuously to about 14.6 at 4 mm, and down to about 10, still higher than the curve 224', for delivery filter only for 6 mm thickness.

Finally, curve 242 illustrates the case of the arrangement of FIG. 11f, in which all three of the delivery filter, collection filter, and sidewall mirror elements are used, with an enhancement factor 242' falling more slowly than curve 238' as the sample thickness increases, to a factor of about 12 at 6 mm thickness.

Overall, for a thicker sample, the single most beneficial enclosure element is the delivery filter. For thinner samples, the additional benefits of using the collection filter are very significant, but reduce with increased sample thickness as the proportion of probe photons reaching the far side of the sample diminishes.

Figure 14A:
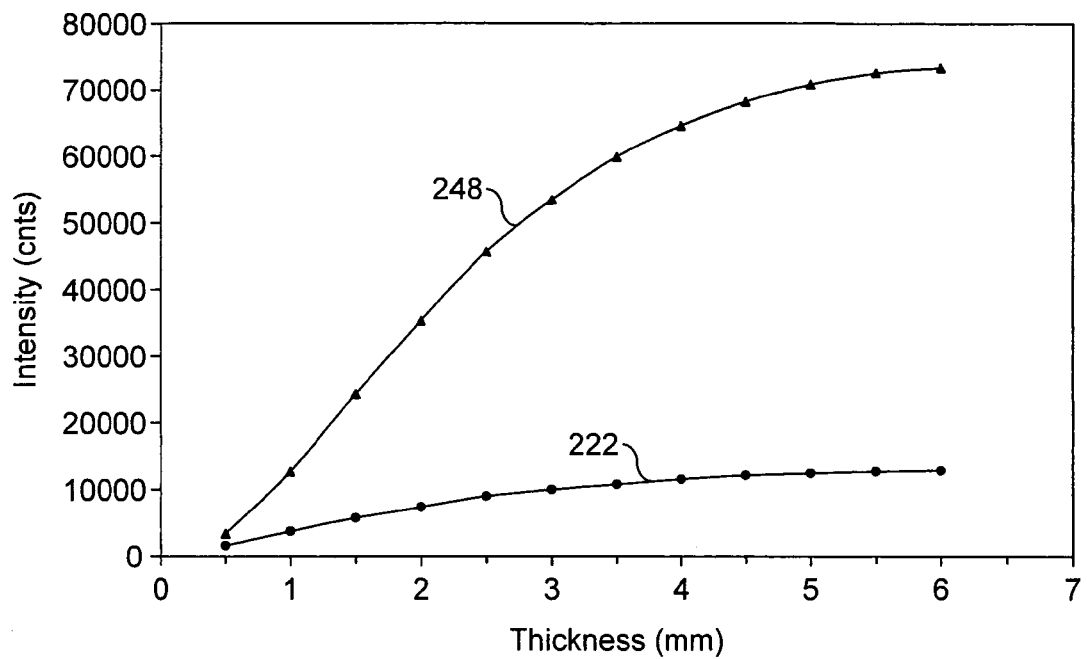
Figure 14B:
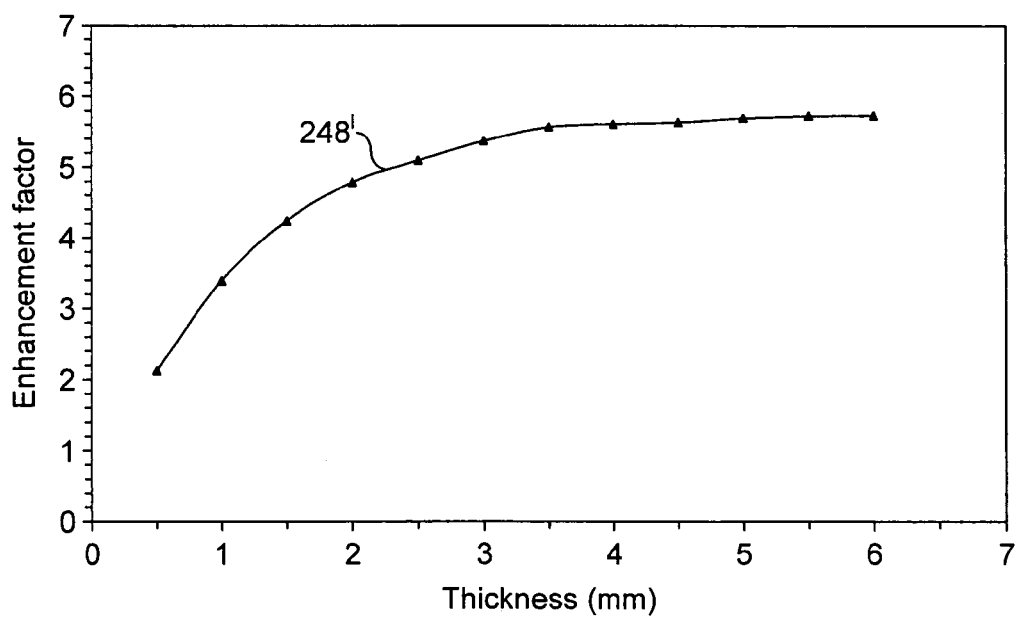

Results of Monte Carlo simulations for the backscattering geometry are shown in FIG. 14a. Curve 222, representing the count of Raman photons emerging from the upper surface of the sample using no optical enclosure elements, has already been shown in FIG. 12a. Curve 248 is for the same backscattering geometry, but with a combined delivery/collection filter placed against the top surface of the sample. This arrangement is therefore the same as shown in FIG. 11a, except that the filter is defined to allow all Raman scattered photons to exit, while returning 95% of the probe photons back into the sample. Filter characteristics which could be used to achieve this or similar performance are shown in FIGS. 7a and 7b. For a 4 mm thick sample, the enhancement factor over the bare sample results of curve 222 is about 5.6, as illustrated in the enhancement factor curve 248' of FIG. 14b.

The compromises of using an filter having an edge characteristic to pass Raman scattered photons while blocking the majority of scattered probe photons were mentioned in the discussion of FIG. 5 above. Essentially, the edge must be far enough beyond the probe wavelength to reflect scattered probe photons incident at shallow angles, without blocking desired Raman wavelength photons. The enhancement factor for a 4 mm thick sample has been calculated for a probe wavelength of 830 nm and a dielectric filter having the frequency dependence of FIG. 3 for an edge characteristic lying (for normal incidence) between the probe wavelength and the Raman wavelength. For an edge lying at each of 1000, 2000 and 3000 cm$^{-1}$ above the probe wavelength, the enhancement factor is calculated to be 1.8, 2.8 and 4.3.

Figure 15:
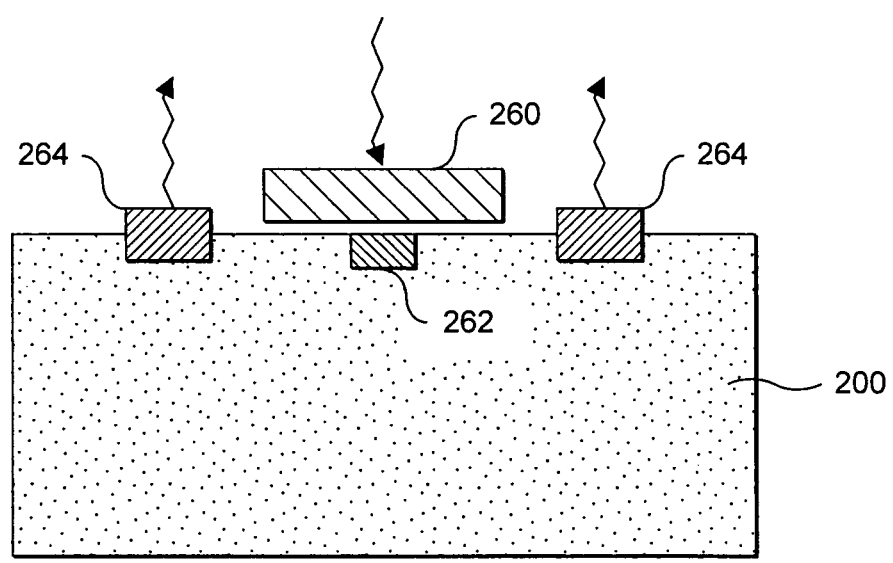

In a further Monte Carlo experiment the sample arrangement of FIG. 15 was used. The cylindrical sample 206 is the same as that of FIG. 11a. A delivery filter 260 is placed adjacent to the upper surface, but covers only a central, circular interface region which has a diameter of 4 mm, centred on a probe beam deposition region 262 with a diameter of 1 mm. The delivery filter 260 is characterised by reflecting back into the sample 95% of the probe and Raman scattered photons which would otherwise escape. Raman scattered photons emerging from the upper surface of the sample in an annular collection region 264 having inner and outer diameters of 6 mm and 8 mm, centred on the probe beam deposition region 262, were counted.

Figure 16A:
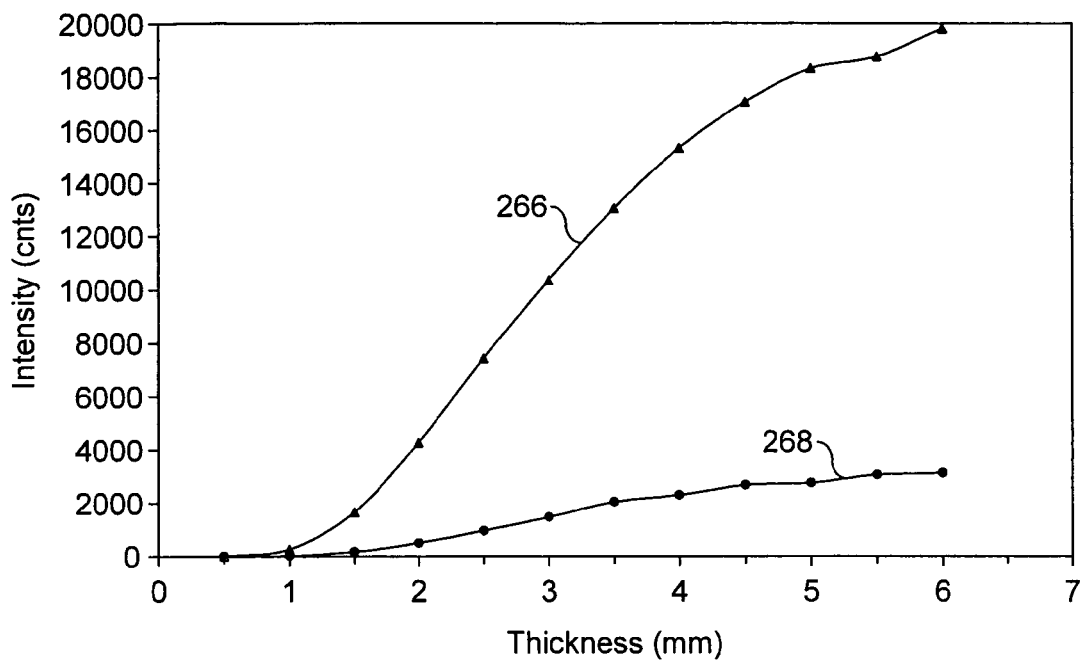
FIGS. 16a and 16b show calculated intensities using the geometry of FIG. 15, and related enhancement factors.
Figure 16B:
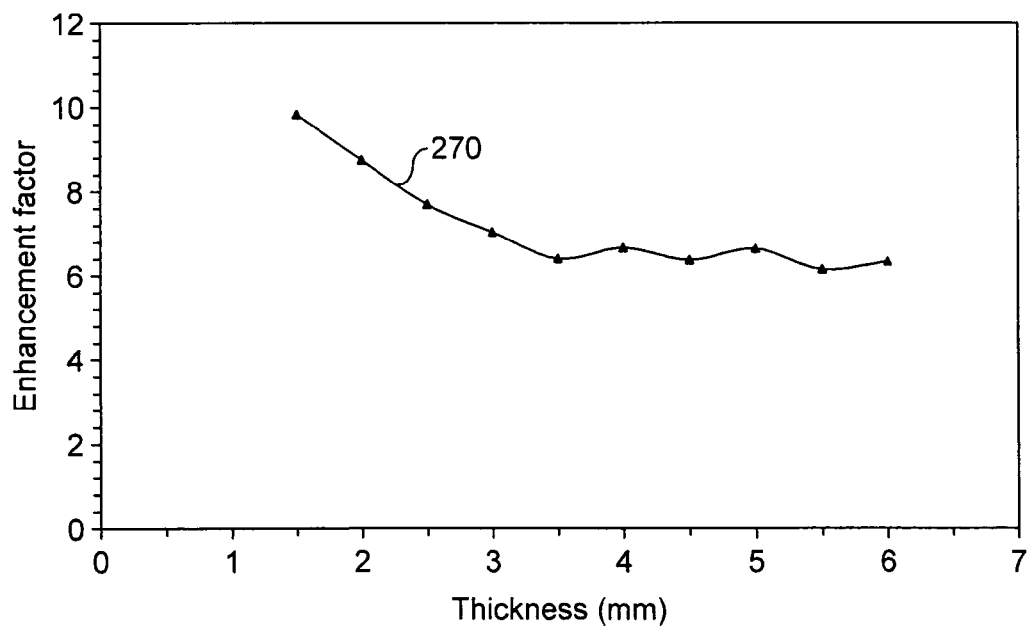

The counts of Raman photons emerging through the annular collection region 264 are shown for a variety of thicknesses of the sample 200 in FIG. 16a, as curve 266. The counts for a corresponding experiment but omitting the delivery filter 260 are shown as curve 268. The ratio of these curves is shown as an enhancement factor, showing the benefit of using the delivery filter for a variety of sample thicknesses, in FIG. 16b (curve 270). For a 4 mm thick sample the enhancement factor is 6.7.

The configuration of FIG. 15 is similar to that already discussed in connection with FIG. 9a. In one alternative to the configuration of FIG. 15, an annular delivery filter and deposition region may surround a central collection region. A variety of other delivery and collection geometries to which the delivery and collection filter elements described herein can be applied are discussed, for example, in WO2006/061566, the content of which is incorporated herein by reference.

Figure 17:
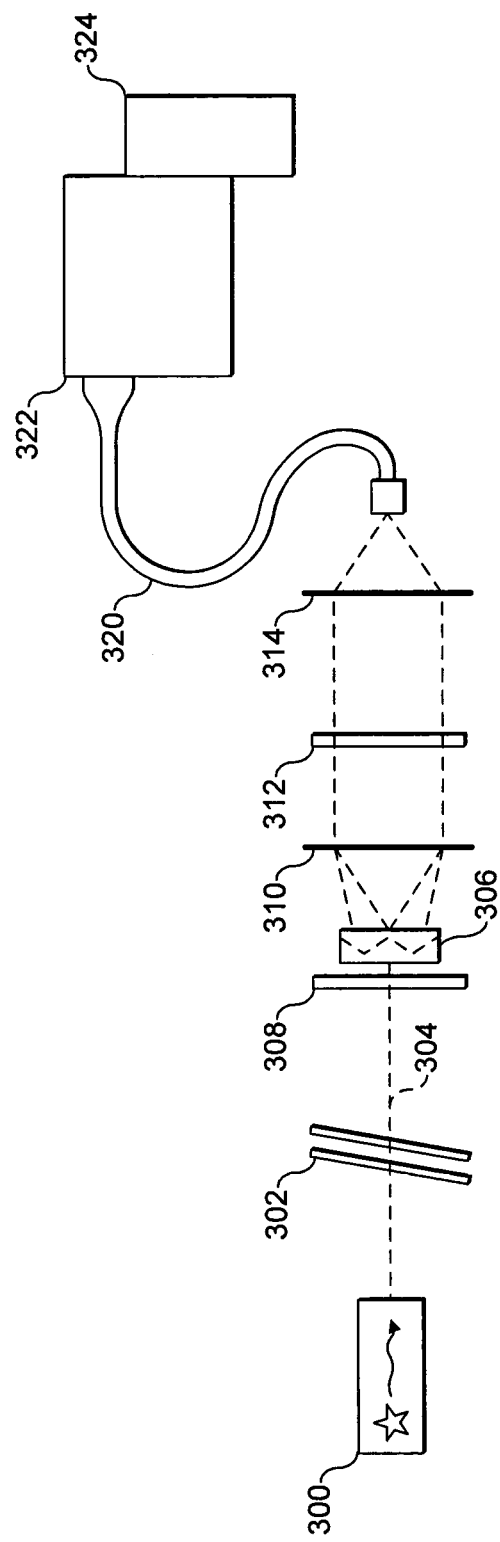
FIG. 17 schematically shows a laboratory optical arrangement used to demonstrate the invention.

Laboratory experiments were also carried out to demonstrate the invention, using apparatus illustrated schematically in FIG. 17. A probe beam 304 was generated using an attenuated 115 mW temperature stabilised diode laser 300 for Raman spectroscopy operating at 827 nm (micro Laser Systems, Inc, L4 830S-115-TE). The beam was spectrally purified by removing any residual amplified spontaneous emission components from its spectrum using two 830 nm bandpass filters 302 (Semrock). These were slightly tilted to optimise their throughput for the 827 nm laser wavelength. The sample 306 was provided by a standard paracetamol tablet having a diameter of 12.8 mm and a thickness of 3.8 mm, arranged such that the probe beam was perpendicularly incident at the centre of a circular face of the tablet, after passing through an adjacent delivery filter. The laser power at the sample was 50 mW and the laser spot diameter was ~4 mm. The beam was polarised horizontally at the sample.

Raman light was collected from the opposite side of the sample using a 50 mm diameter lens 310 with a focal length of 60 mm. The scattered light was collimated and passed through a 50 mm diameter holographic notch filter 312 (830 nm, Kaiser Optical Systems, Inc) to suppress the elastically scattered component of light. The filter was also slightly tilted to optimise the suppression at 827 nm. A second lens 314, identical to the first one, was used to image, with magnification 1:1, the sample collection zone onto the front face of a fibre probe 320 made of 22 active optical fibres. The individual fibres were made of silica with a core diameter of 220 μm, a doped silica cladding diameter of 240 μm and a polyimide coating of 265 μm diameter. The fibre numerical aperture was 0.37. The bundle was custom made by CeramOptec Industries, Inc. The fibre bundle length was about 2 m and at the output end the fibres were arranged into a linear shape oriented vertically and placed in the input image plane of a Kaiser Optical Technologies Holospec 1.8i NIR spectrograph 322. The Raman spectra were collected using a NIR back-illuminated deep-depletion TE cooled CCD camera 324 (Andor Technology, DU420A-BR-DD, 1024×256 pixels) by binning the entire chip vertically. The spectra were not corrected for the variation of detection system sensitivity across the spectral range.

The delivery filter 308 placed over the laser beam deposition area on the sample was a 25 mm diameter Semrock dielectric bandpass filter centred at 830 nm with bandwidth of 3.2 nm (LL01-830-25, MaxLine Laser-line Filter). The slight mismatch between the laser wavelength (827 nm) and the filter wavelength was compensated by introducing a small tilt to the incident beam at sample 306. Although the mismatch somewhat reduced the effectiveness of the delivery filter element a substantial enhancement of the Raman signal was still present.

Figure 18A:
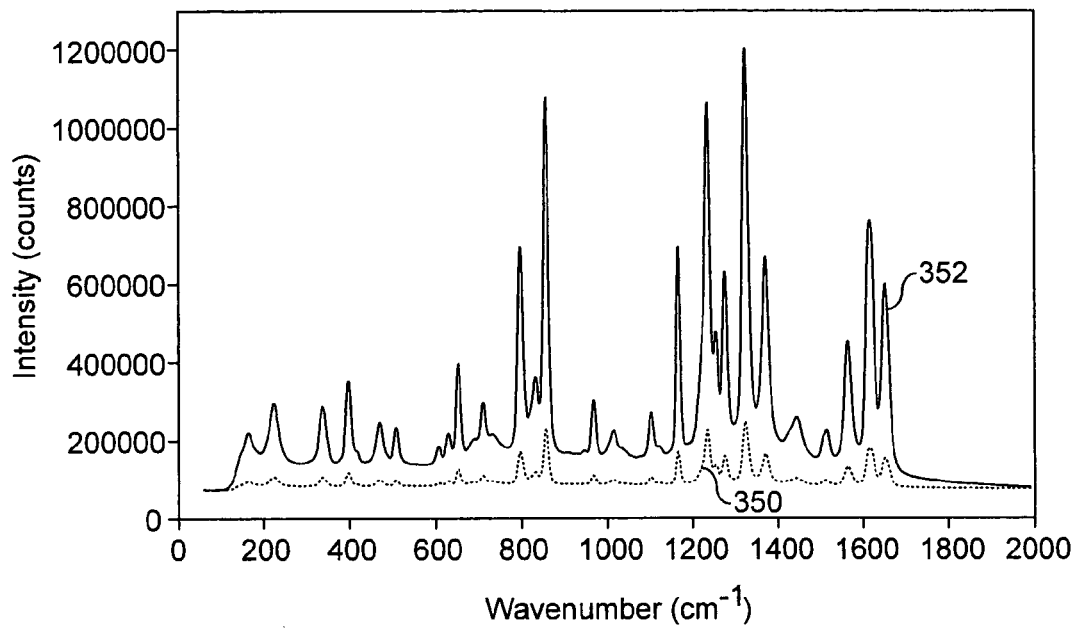
FIGS. 18a and 18b show Raman spectra measured using the apparatus of FIG. 17.
Figure 18B:
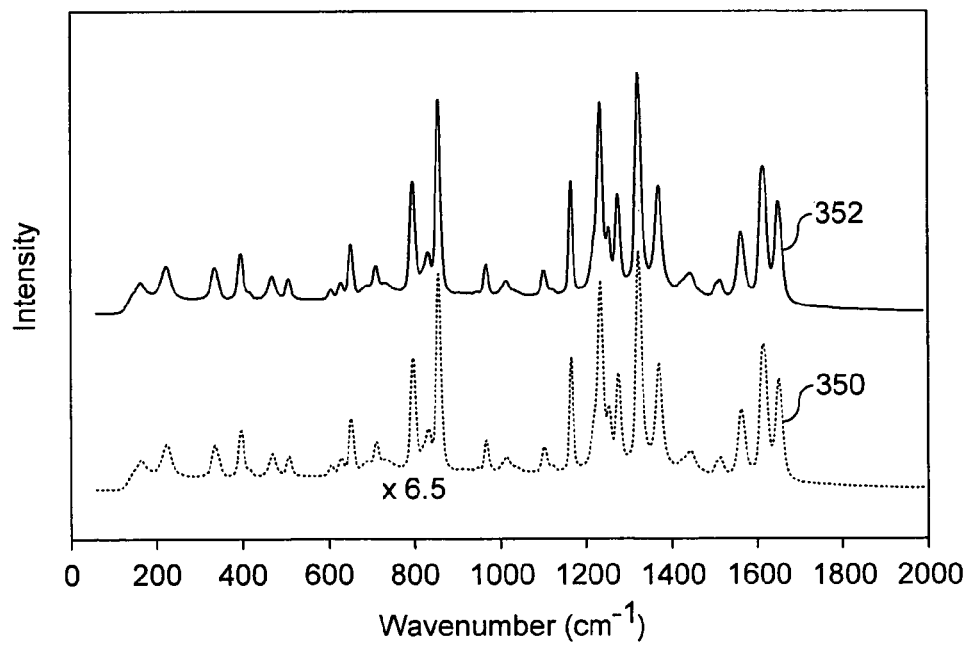

Raw photon count data from the CCD camera 324 using the above arrangement is plotted over a range of wavelength difference from the laser frequency in FIG. 18a. The lower curve 350 is for the experiment with delivery filter 308 omitted, and the upper curve 352 is for when the delivery filter was in place, in each case for the same exposure time of 10 seconds. In FIG. 18b the same data is shown, but with the vertical scale of curve 350 expanded by a factor of 6.5. It can be seen that a uniform enhancement factor of about 6.5 is achieved by the additional use of the delivery filter across the whole spectral range.

The experimental enhancement is less than the value of 9.4 found for the corresponding numerical Monte Carlo experiment, but this may easily be accounted for in differences in scattering lengths between the modelled and real samples, as well as the slight mismatch between the laser and delivery filter wavelengths. Nevertheless, the enhancement factor is still very high.

Importantly, the enhancement exhibited good reproducibility upon subsequent remounting of the delivery filter adjacent to the tablet, and no temporal fluctuation was observed when the filter was in place. Also, the enhancement was uniform across the Raman spectra measured, which may be important in applications involving complex analytes where the spectral pattern serves as a means of identifying multiple individual components, as well as determining relative concentrations.

Although the invention has generally been illustrated with embodiments in which Raman spectroscopy of a sample is required, it may more generally be applied to any circumstances in which retention of incident light within a scattering medium is required. In some embodiments, for example, no collection or analysis of the scattered light is required.

Figure 19:
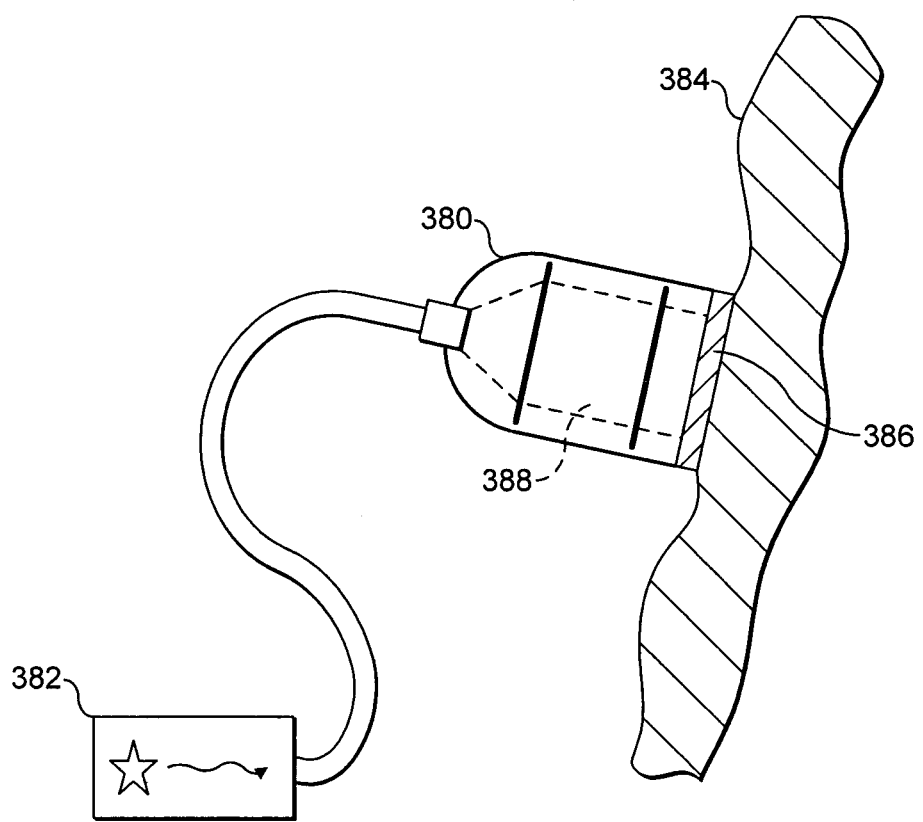
FIG. 19 illustrates an optical delivery device embodying the invention.

FIG. 19 illustrates an optical head 380 for delivering light generated using laser 382 into a human or animal patient 384, for example to trigger a chemical reaction involving a substance introduced into the patient, as known in various photodynamic therapies. The use of a delivery filter 386 adjacent to the surface of the patient, in conjunction with collimator 388' preferentially retains the introduced light within the patient, allowing very much lower laser powers to be used.

A particular application is in photo-thermal therapies such as photo-thermal cancer therapies, in which electromagnetic radiation is delivered to tissue containing absorbing bodies. In recent research, near-infrared radiation is delivered to tissues containing appropriately formed nanoparticles, for example see Gobin et al., Nano Lett., 7(7), 1929-1934, 2007. The present invention provides an improved method of carrying out photo-thermal therapy by directing the radiation, typically laser radiation, into tissue through a delivery filter as described herein, thereby increasing the intensity of the radiation within the tissue without needing to increase the power of the incident beam.

Other applications include NIR absorption or fluorescence optical tomography and spectroscopy.

A diffusely scatting sample may be defined, for example, as a sample within which the typical path length between scattering events of a photon of the relevant incident light is much less than the size of the sample, for example at least ten times, and more preferably at least a hundred times less than a characteristic size of the sample (such as the thickness in the axis of the incident light beam), such that the directional structure of an incident light beam is very quickly lost.

A variety of changes and modifications may be made to the described embodiments without departing from the scope of the invention as defined by the appended claims.

The invention claimed is:

1. A method comprising:
   locating a delivery filter adjacent to a diffusely scattering sample; and
   directing a beam of incident light of a predetermined wavelength through the delivery filter at a beam angle of incidence, and to the sample,
   the delivery filter having characteristics such that reflection of said incident light is dependent upon angle of incidence of said light at the filter, and such that at least 50% of the incident light of the predetermined wavelength which is diffusely scattered back out of the sample to arrive at the delivery filter is reflected by the delivery filter back towards the sample.

2. The method of claim 1 wherein the delivery filter is adapted to reflect light of said predetermined wavelength more strongly when incident at shallower angles of incidence.

3. The method of claim 1 wherein reflection of said incident light by the delivery filter increases at angles of incidence higher than said beam angle.

4. The method of claim 1 wherein the filter characteristics have an incident light transmission feature, which is coincident with the wavelength of the incident light at the beam angle of incidence, and which shifts to shorter wavelengths for increasing angles of incidence.

5. The method of claim 1 wherein the filter characteristics have an incident light reflection feature at longer wavelengths than the wavelength of the incident beam at the beam angle of incidence, and which shifts to shorter wavelengths to cover the beam wavelength at higher angles of incidence.

6. The method of claim 1 wherein the beam at the delivery filter is collimated or semi-collimated.

7. The method of claim 1 wherein the delivery filter is a multi-layer dielectric filter.

8. The method of claim 1 wherein the delivery filter is a holographic filter.

9. The method of claim 1 wherein the delivery filter is spaced from the sample by a distance which is less than a diameter of the incident beam at the sample.

10. The method of claim 1 wherein the delivery filter is spaced from the sample by a distance which is less than a diameter of the delivery filter.

11. The method of claim 1 wherein the delivery filter is spaced from the sample by a distance which is less than a diameter of the sample.

12. The method of claim 1 wherein the delivery filter is curved so as to be adapted to conform to a curved surface of the sample covered by the filter.

13. The method of claim 1 further comprising providing a diffusely scattering spacer element between a surface of the sample to be covered, and the delivery filter.

14. The method of claim 13 wherein the spacer element is deformable so as to adapt to a curved surface of the sample.

15. The method of claim 13 wherein the spacer element is provided with anisotropic scattering characteristics.

16. The method of claim 1 further comprising providing a peripheral mirrored guide surrounding a space between the delivery filter and the surface of the sample covered, so as to retain diffusely scattered light which would otherwise escape around the edge of the covered area.

17. The method of claim 1 further comprising collecting light scattered out of the sample, and analysing said light to detect the strength of one or more spectral wavelength features of said collected light.

18. The method of claim 17 wherein said one or more spectral wavelength features are Raman scattering features.

19. The method of claim 17 wherein the collected light is collected after scattering away from the sample and then passing through the delivery filter.

20. The method of claim 17 wherein the collected light is collected after scattering away from the sample and through a collection filter separate from said delivery filter.

21. The method claim 1 wherein the delivery filter has a transmission edge which lies to one side of the predetermined wavelength of the incident light at less than 10 degrees from perpendicular to the delivery filter, thus permitting the incident beam to pass, and which lies to the other side of the predetermined wavelength of the incident light at shallower angles of incidence greater than 30 degrees from perpendicular to the delivery filter, thus reflecting back diffusely scattered lighter emerging from the sample.

22. The method of claim 1 wherein the sample is a diffusely scattering object.

23. The method of claim 22, wherein the sample is a pharmaceutical tablet.

24. An optical enclosure for enhancing the intensity of incident light of a predetermined wavelength within a diffusely scattering sample, the optical enclosure comprising a delivery filter through which a beam of said incident light of the predetermined wavelength is directed to the sample at a beam angle of incidence with respect to said filter,
   the delivery filter having characteristics such that reflection of said incident light of the predetermined wavelength increases at angles of incidence away from the beam angle of incidence, and such that at least 50% of the incident light of the predetermined wavelength which is scattered diffusely from the sample to arrive at the delivery filter is reflected back into the sample by the delivery filter.

25. The optical enclosure of claim 24 wherein the characteristics of the delivery filter are such that the reflection of said incident light increases at increasing angles of incidence.

26. The optical enclosure of claim 24 wherein the characteristics of said delivery filter include a transmission region which shifts to shorter wavelengths than the incident light for higher angles of incidence.

27. The optical enclosure of claim 24 wherein the delivery filter has a shorter wavelength transmission edge feature, the wavelength of said edge feature shifting to shorter wavelengths with increasing angles of incidence, such that the incident light is transmitted at the beam angle of incidence, and significantly reflected at a range of higher angles of incidence.

28. The optical enclosure of claim 24 wherein the delivery filter is a band pass filter having a band pass wavelength region matched to the predetermined wavelength and beam angle of incidence of said beam of incident light.

29. The optical enclosure of claim 24 wherein the delivery filter is a notch filter having a blocking wavelength region matched to block the incident light at a range of beam angles greater than the angle of incidence of said beam of incident light.

30. The optical enclosure of claim 24 wherein said delivery filter is adjacent to said sample.

31. The optical enclosure of claim 30 wherein the delivery filter is spaced from the sample by a distance which is less than a diameter of the sample.

32. The optical enclosure of claim 24 wherein the delivery filter is curved so as to conform to a curved sample surface to be covered by the filter.

33. The optical enclosure of claim 24 further comprising a diffusely scattering spacer element arranged between the delivery filter and a curved surface of the sample.

34. The optical enclosure of claim 33 wherein the spacer element is deformable so as to adapt to a curved surface of the sample.

35. The optical enclosure of claim 33 wherein the spacer element is provided with anisotropic scattering characteristics.

36. The optical enclosure of claim 24 further comprising a peripheral mirrored guide surrounding a space between the delivery filter and the surface of the sample to be covered, so as to retain diffusely scattered light which would otherwise be lost between the sample and the filter.

37. The optical enclosure of claim 24 wherein the delivery filter is a dielectric multilayer filter or a holographic filter.

38. The optical enclosure of claim 24 further comprising a collection filter which reflects incident light elastically scattered out of the sample back towards the sample, but transmits incident light inelastically scattered within the sample so as to have a different wavelength from the predetermined wavelength said incident light.

39. The optical enclosure of claim 38 wherein the inelastic scattering is Raman scattering by the diffusely scattering sample to longer wavelengths than the predetermined wavelength incident light.

40. The optical enclosure of claim 38 wherein the collection filter comprises a long wavelength pass filter having an edge lying between the predetermined wavelength of the incident light and portions of the inelastically scattered incident light for subsequent detection.

41. The optical enclosure of claim 24 wherein the characteristics of the delivery filter further comprises a transmission feature matched to transmit portions of the inelastically scattered incident light for subsequent detection.

42. The optical enclosure of claim 24 further comprising one or more mirror surfaces arranged across parts of the sample not covered by the delivery filter, to reflect light scattering out of the sample back into the sample.

43. Apparatus comprising the optical enclosure of claim 24, the apparatus being for detecting spectral features of a diffusely scattering sample, the apparatus further comprising:
an incident light source adapted to form said incident light beam;
delivery optics arranged to direct said incident light beam through said delivery filter and to said sample;
collection optics arranged to collect light scattered from said sample; and
a detector arranged to detect one or more characteristics of the spectrum of said collected light.

44. Apparatus for detecting one or more spectral characteristics of a diffusely scattering sample, comprising
a delivery filter adapted to allow a beam of incident light of predetermined wavelength to pass through at an incident beam angle of incidence to reach the sample, wherein the delivery filter is a multi-layer dielectric filter having a transmission characteristic coincident with the predetermined wavelength of the incident light beam at said angle of incidence, but which shifts to shorter wavelengths at higher angles of incidence such that the filter preferentially reflects back towards the sample incident light of the predetermined wavelength which is diffusely scattered from the sample; and
the diffusely scattering sample,
the apparatus being arranged such that at least 50% of the incident light of the predetermined wavelength scattered back from the sample to reach the delivery filter is reflected back towards the sample.

45. The apparatus of claim 44 wherein the delivery filter is positioned within a distance from the sample which is less than a diameter of the filter.

46. The apparatus of claim 44 wherein the incident beam has a beam diameter, and the delivery filter is positioned within a distance from the sample which is less than the incident beam diameter.

47. The apparatus of claim 44 wherein the delivery filter is arranged to cover a region of the sample.

48. A method of illuminating a diffusely scattering sample, comprising:
covering a region of the sample with a delivery filter; and
directing a beam of collimated light of a predetermined wavelength through the delivery filter and into said sample,
wherein said delivery filter is adapted to reflect back to the sample at least 50% of the light of said predetermined wavelength diffusively scattered out of the sample to said delivery filter in said region.

49. The method of claim 48 wherein the delivery filter has transmission and/or reflection characteristics which shift to shorter wavelengths at shallower angles of incidence.

50. The method of claim 48 wherein the delivery filter characteristics have a transmission region coincident with the predetermined wavelength at a first range of angles of incidence, and is shifted away from the predetermined wavelength at a second range of angles of incidence.

51. The method of claim 48 wherein the delivery filter characteristics have a transmission region coincident with the predetermined wavelength at substantially normal angles of incidence.

* * * * *